(12) United States Patent
Cartier et al.

(10) Patent No.: US 7,544,202 B2
(45) Date of Patent: Jun. 9, 2009

(54) RETRIEVABLE BLOOD CLOT FILTER

(75) Inventors: William A. Cartier, Hampton, NY (US); Giorgio di Palma, Queensbury, NY (US)

(73) Assignee: AngioDynamics, Inc., Queensbury, NY (US)

( * ) Notice: Subject to any disclaimer, the term of this patent is extended or adjusted under 35 U.S.C. 154(b) by 291 days.

(21) Appl. No.: 10/991,041

(22) Filed: Nov. 16, 2004

(65) Prior Publication Data

US 2005/0288704 A1   Dec. 29, 2005

Related U.S. Application Data

(60) Provisional application No. 60/583,274, filed on Jun. 25, 2004, provisional application No. 60/614,757, filed on Sep. 29, 2004.

(51) Int. Cl.
*A61M 29/00* (2006.01)
(52) U.S. Cl. .................................................. 606/200
(58) Field of Classification Search ............... 606/151, 606/200, 198; 623/1.1, 1.24
See application file for complete search history.

(56) References Cited

U.S. PATENT DOCUMENTS

| | | | | |
|---|---|---|---|---|
| 4,494,531 A * | 1/1985 | Gianturco | ................ | 606/200 |
| 4,832,055 A * | 5/1989 | Palestrant | ................ | 128/899 |
| 6,273,901 B1 * | 8/2001 | Whitcher et al. | ................ | 606/200 |
| 6,306,163 B1 * | 10/2001 | Fitz | ................ | 623/1.12 |
| 6,331,183 B1 * | 12/2001 | Suon | ................ | 606/200 |
| 6,391,045 B1 * | 5/2002 | Kim et al. | ................ | 606/200 |
| 6,506,205 B2 * | 1/2003 | Goldberg et al. | ................ | 606/200 |
| 2003/0208227 A1 * | 11/2003 | Thomas | ................ | 606/200 |
| 2003/0208253 A1 * | 11/2003 | Beyer et al. | ................ | 623/1.1 |
| 2003/0212432 A1 * | 11/2003 | Khairkhahan et al. | ................ | 606/200 |
| 2004/0230220 A1 * | 11/2004 | Osborne | ................ | 606/200 |

* cited by examiner

*Primary Examiner*—(Jackie) Tan-Uyen T. Ho
*Assistant Examiner*—Melanie Tyson
(74) *Attorney, Agent, or Firm*—Harry K. Ahn; Abelman Frayne & Schwab

(57) ABSTRACT

A compact retrievable blood clot filter and a method of retrieving the filter. The retrievable filter has a primary hub, a set of filter struts having a conical configuration and extending from the primary hub, and a set of alignment struts connected to the filter struts to provide centering of the filter. A set of control struts connected to the alignment struts has a secondary hub which is axially movable relative to the primary hub. Movement of the secondary hub causes the control struts to pull the alignment struts radially inward into a retractable state for retrieval of the filter.

35 Claims, 18 Drawing Sheets

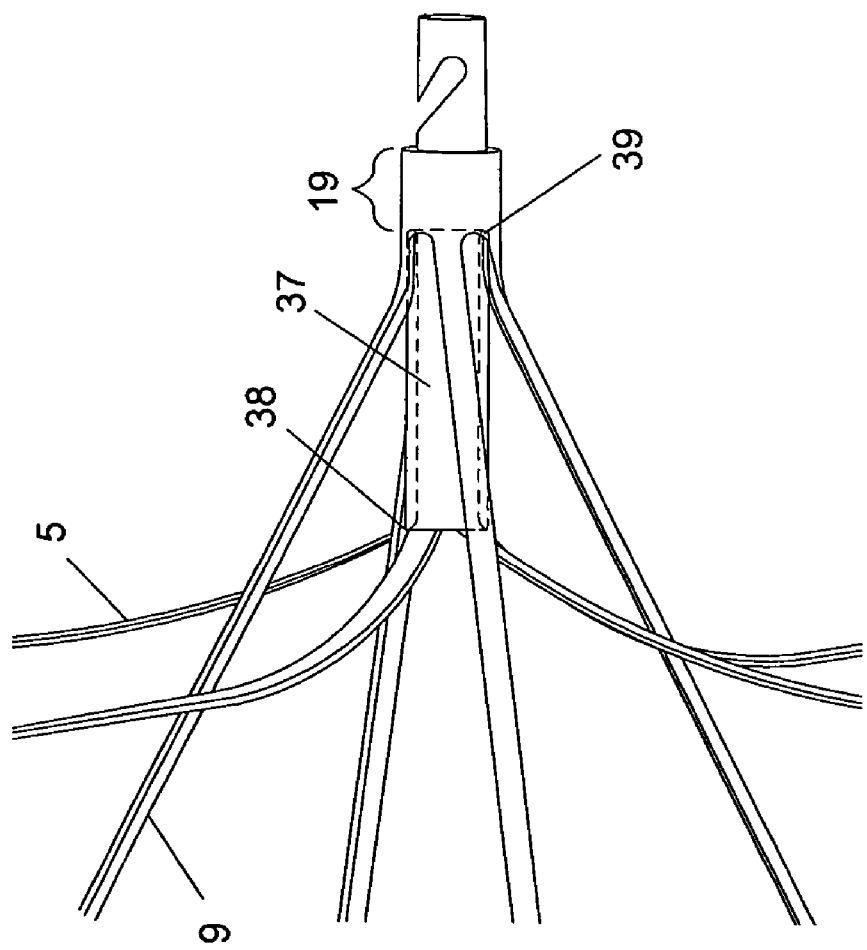

RETRIEVABLE BLOOD CLOT FILTER

CROSS REFERENCE TO RELATED APPLICATIONS

This application claims priority under 35 U.S.C. §119 (e) to U.S. Provisional applications, Ser. Nos. 60/583,274, filed Jun. 25, 2004, and 60/614,757 filed Sep. 29, 2004, which are incorporated herein by reference.

FIELD OF THE INVENTION

The present invention relates to a medical device apparatus and method for the capturing of thrombus. More particularly, the present invention relates to a retrievable vena cava filter device for the capture of blood clots and method of manufacture of the device, and the method of deployment and retrieval of the device.

BACKGROUND OF THE INVENTION

Vena cava filters are used to capture potentially fatal pulmonary emboli at an anatomical location where they may pose less risk of pulmonary emboli for the patient. Since the vast majority of pulmonary emboli originate from the lower body, filters are mainly placed in the inferior vena cava.

Vena cava filters have been in use since the 1960s in a variety of configurations. Early filters required open surgical placement (Mobin—Uddin Filter; Kimray—Greenfield filter). Since the late 1970s, improvements in delivery were made and numerous filters were developed for minimally invasive percutaneous placement. These filters included the Greenfield filter, the Gianturco Bird's Nest Filter, the Vena Tech LGM filter, the Simon Nitinol Filter and others. More recently, filters have been developed and marketed with the capability of retrieval after relatively long terms of implantation, which include the Bard Recovery Filter, the Cordis Optease Filter and the Cook Tulip Filter.

Although addressing some desirable characteristics of a filter, the majority of the IVC filters presently on the market do not satisfy other desirable characteristics of an ideal filter. The ideal device should capture blood clots while ensuring continued blood flow through the vessel. Blood flow disruption and turbulence often leads to thrombus formation and buildup at and around the filter. Studies have demonstrated that a conical filter configuration provides the optimal filtering efficiency. Filtering efficiency, for the purposes of this invention can be defined as the capability of the device to capture and retain clots of a pre-determined size, the ability to maintain blood flow through the filter in the presence of captured clots, and the capability of dissolving or lysing the clots caught in the filter. Conical designs force clots toward the center of the filter, allowing blood flow passage around the clot. Continued blood flow through the filter when a clot load is present ensures that captured clots are exposed to the lysing action of the blood flow.

Although conical filter configurations currently available on the market provide optimal filtering capabilities, these designs are prone to tilting and misalignment. When not in proper alignment, filtering ability is compromised. The central conical portion of the filter may tilt to the extent that it becomes embedded in the vessel wall. With retrieval designs, the retrieval hook is typically located at the central apex of the cone. If the tilting results in the retrieval hook coming in contact with the vessel wall, retrieval efforts become difficult or may even prevent removal. Laminar blood flow is disturbed, effective lysing of capture clots decreases, and thrombus build-up occurs.

To address the misalignment problem, filtering cones have been designed with alignment mechanisms to prevent tilting. For example, stent-like cage constructions have been designed to prevent the conical filter from becoming misaligned. The stent-like cage rests up against the vessel wall providing alignment to the filtering conical portion of the filter. This design, while optimizing centering of the filter, cannot be easily retrieved because of the difficulty in snaring and collapsing the cage. An example of this type of filter design is the Vena Tech LP filter which has a conical filtering segment adjoined to a zigzag stent base configuration for centering the cone within the vessel. Although this type of design combines the optimal filtering characteristics of a conical configuration with a non-tilting base, the device is not retrievable. The struts of the non-tilting base become incorporated into the vessel wall and cannot be easily disengaged and removed using standard snare removal techniques. The location of the stabilizing struts prevents the ability to withdraw the device into a sheath for removal.

It is possible to build a simple centering cage base/cone filter design that is retrievable by attaching the base to the filter segment in series. This design, while retrievable, is not practical due to the increased length of the device. The desired length of a typical IVC filter is between 3 and 5 centimeters. Longer lengths are undesirable because of the limited implantation space of the vena cava. For example, in some cases it is necessary to deploy a second filter due to malfunction of the initially placed filter. Shortening the filter segment may make the overall device length acceptable, but may result in sub-optimal filter strut angles. Alternatively, shortening the centering cage segment may compromise the alignment function of the device.

IVC filters should be capable of remaining in the vessel for long periods of time, and in some cases, indefinitely. The filter should be designed so as not to migrate from its originally deployed position while still allowing for retrieval of the filter. Thus the vessel wall engagement mechanism should be designed so as to maintain position even under a heavy clot load and yet allow easy and atraumatic disengagement from the vessel during retrieval. Longitudinal movement of the filter has traditionally been prevented by configuring filter ends with hooks that embed in the vessel wall.

Because of concerns with permanent implantation of filters, including possible migration and structural integrity over long time periods, there is an emerging trend for filters that can optionally be retrieved after a specified period of time. The optimal retrievable filter should have wall-engaging mechanism that is sufficient to ensure that the device does not migrate in either direction while implanted. The wall-engaging mechanism should also be designed to allow percutaneous removal of the device without significant trauma or damage to the vena cava wall even after neointima overgrowth has occurred. These two disparate clinical requirements, long-term fixation and atraumatic removal, are difficult to achieve in a single filter design. Some prior art filter designs have utilized aggressive anchoring mechanisms to ensure fixation, but these designs are difficult to remove. Conversely, designs that limit wall contact are easier and less traumatic to disengage from the vessel, but may be more prone to migration.

As with all long-term or permanent implant device, the optimal device design will maintain structural integrity of the device for the duration of implantation. Although rare, filter fractures have potentially fatal complications including filter migration into the right atrium and pulmonary embolism caused by compromised filtering efficiency. The ideal filter device should have minimal connection or attachment points which are more susceptible to fatigue over extended periods of time. In addition to long term performance characteristics, it is desirable to provide an IVC filter that is simple and inexpensive to manufacture without requiring complicated assembly processes that might compromise the long-term integrity of the device or increase the overall cost of the device.

Another desirable characteristic of the ideal filter is a small deployment and retrieval system. A design that minimizes the delivery device diameter will result in a smaller insertion site and reduced risks of bleeding, site thrombus and other complications of percutaneous punctures. The ideal vena cava filter should not only be easy to deploy using minimally invasive percutaneous techniques, but also be repositionable during initial deployment. Many filters are designed for ease of deployment but do not allow for repositioning during delivery.

SUMMARY OF THE DISCLOSURE

A compact retrievable blood clot filter has a primary hub, a set of filter struts having a conical configuration and extending from a primary hub, and a set of alignment struts connected to the filter struts to provide centering of the filter. A set of control struts connected to the alignment struts has a secondary hub which is axially movable relative to the primary hub. Axial movement of the secondary hub relative to the primary hub causes the control struts to pull the alignment struts radially inward into a retractable state for retrieval.

In one aspect of the invention, the filter and alignment struts together are constructed from a single tubular element and provide clot capturing and filter centering functions. The control struts are fabricated from a second tube and functions to control deployment and retrieval. The two tubular elements are slidably coupled to each other in a coaxial arrangement. The device can be easily deployed through a small delivery system, repositioned within the vessel after partial deployment and retrieved. The tubular construction provides a fatigue-resistant device due to the absence of weld joints.

In another aspect of the invention, a method of retrieving the filter is provided. First, the secondary hub is captured. For example, a snare can be used to hook the secondary hub and a sheath is placed over the secondary hub. Then, the captured secondary hub is axially moved relative to the primary hub to pull the alignment struts radially inward. Once the alignment struts are in a retractable state, the sheath is moved over the filter struts relative to the primary hub to enclose the plurality of filter struts. The sheath is then removed along with the captured filter.

BRIEF DESCRIPTION OF THE DRAWINGS

FIG. 3A highlights the conical filter functional component 20 and the non-slotted section 19, FIG. 3B highlights the alignment struts functional component 21, and FIG. 3C highlights the control/connector strut subassembly 3.

FIG. 3D is an enlarged partial plan view of the vena cava filter device in an expanded position showing the position of the inner cannula component 37.

FIG. 11A is a cross-sectional view of the filter within the deployment system prior to deployment in the vein.

FIG. 11B is a plan view of the filter and deployment system with the filtering legs deployed.

FIG. 11C is a plan view of the filter and deployment system with the control struts and the alignment struts deployed.

FIG. 11D is a plan view of the filter and deployment system after the filter has been detached from the deployment system.

FIG. 12A is a plan view of the method of retrieval of the vena cava filter device depicting capture of the device by a snare sheath.

FIG. 12B is a plan view of the method of retrieval of the vena cava filter device depicting the retraction of the non-slotted section 18 of the control strut subassembly 3 into the sheath.

FIG. 12C is a plan view of the method of disengagement of the control struts from the vessel wall in which the control struts are completely collapsed in the center of the vessel.

FIG. 12D is a plan view of the method of retrieval depicting the filter completely collapsed and within the retrieval sheath.

DETAILED DESCRIPTION OF THE INVENTION

Figure 1:
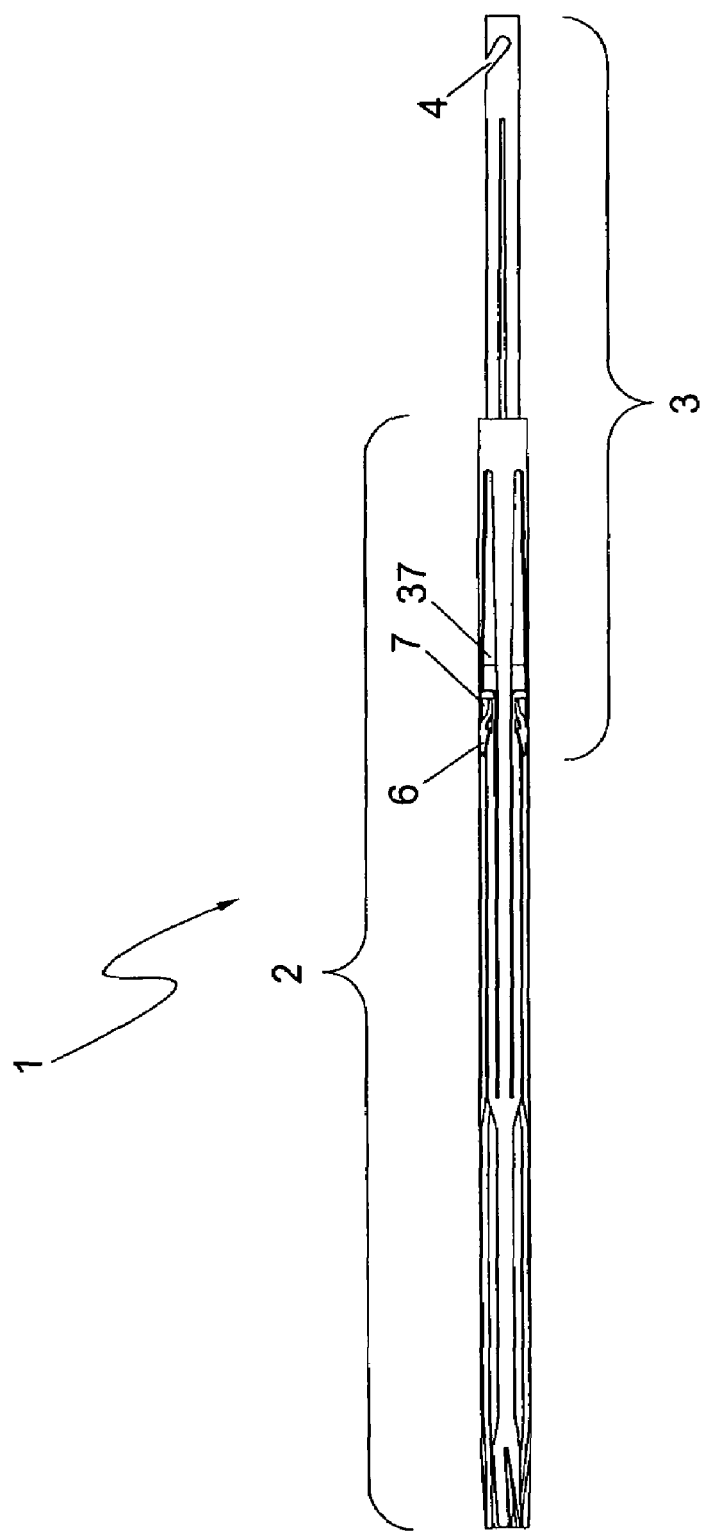
FIG. 1 is plan view of the vena cava filter device of the current invention in a collapsed, non-expanded state.

For the purposes of the present application, the terms upstream and downstream refer to the direction of blood flow. Accordingly, blood flows from an upstream direction towards a downstream direction. Referring to FIG. 1, there is shown an embodiment of the present invention in a plan view of a non-expanded state of the vena cava filter. Although not shown in FIG. 1, the filter 1 is held in a collapsed, non-expanded state by a sheath, catheter or other tubular construct. The filter 1 is comprised of two coaxially arranged tubular subassemblies; a filter cone/alignment strut subassembly 2 and a control strut subassembly 3 which are collapsed to form a slender tubular construct 1 that can be percutaneously inserted through a catheter or sheath into a patient. The filter also includes an inner cannula 37 which is positioned coaxially between subassembly 2 and subassembly 3.

In one aspect of the invention, the filter cone/alignment strut subassembly 2 is formed from one tube, which is of a larger diameter than the second tube forming the control strut subassembly 3. The filter cone/alignment strut subassembly 2 is coaxially positioned around a portion of control strut subassembly 3 in a slideable arrangement. The two tubular subassemblies are interconnected by barbs 6 of the control strut subassembly 3 which are positioned through the barb receiving holes 7 of the outer, filter cone/alignment strut subassembly 2. The control strut subassembly 3 includes a retrieval hook 4 as is well known in the art for facilitating removal of the filter from the body. The inner cannula 37 is fixedly connected to subassembly 2 through a friction fit or other connection means.

Figure 3A:
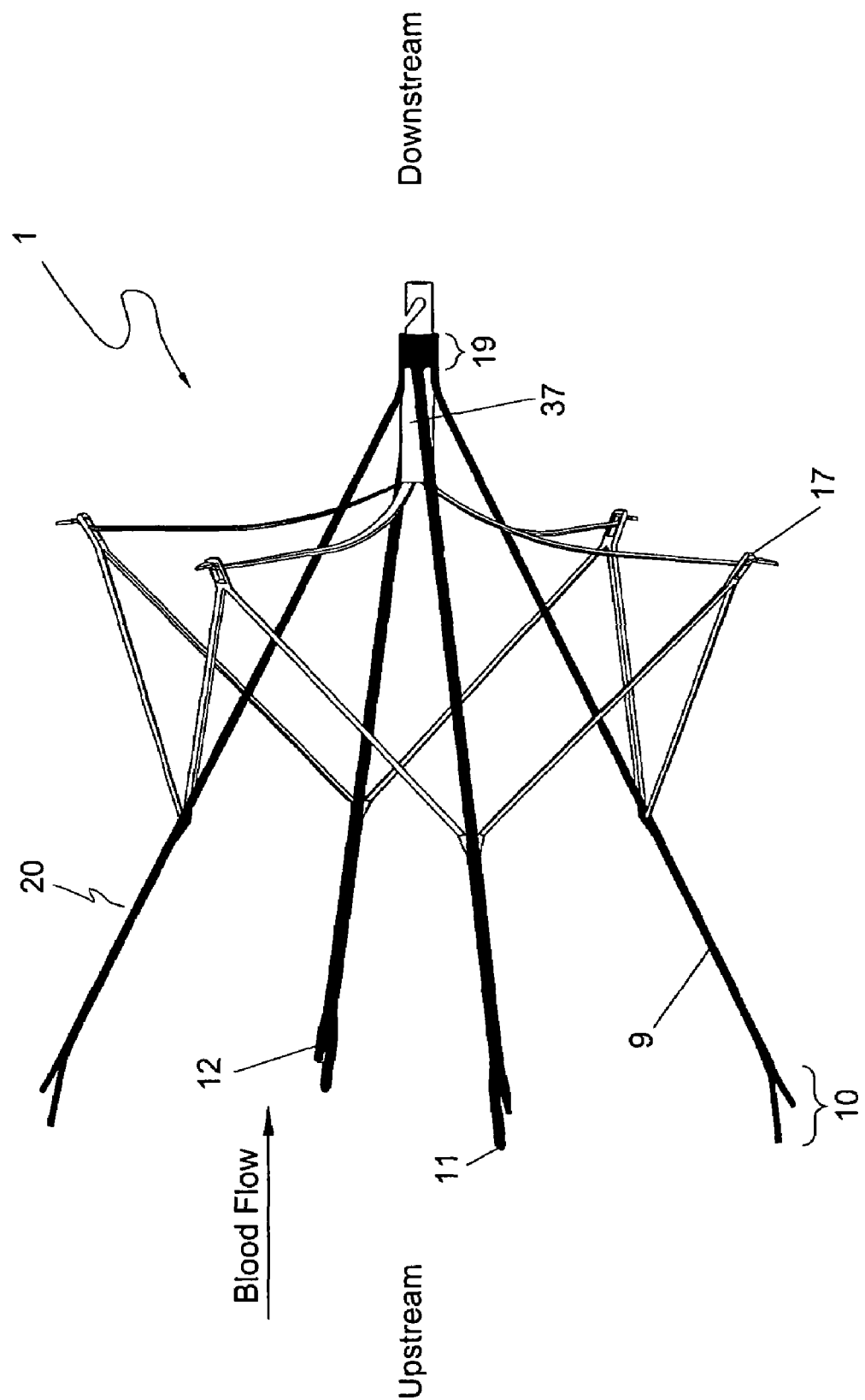
FIG. 3A through FIG. 3C are plan views of the vena cava filter device in a deployed, expanded position with different functional components highlighted in black. Hidden lines have been removed for clarity.

The tubes are preferably of a material with shape-memory characteristics such as nitinol to allow expansion from the collapsed state shown in FIG. 1 to a deployed filter configuration as shown FIG. 3A. Nitinol is an alloy well suited for vena cava filters because of its superelastic characteristics, which enables it to return to a pre-determined expanded shape upon release from a constrained position. Other shape memory metals such as stainless steel may be used to form filter 1.

Figure 5:
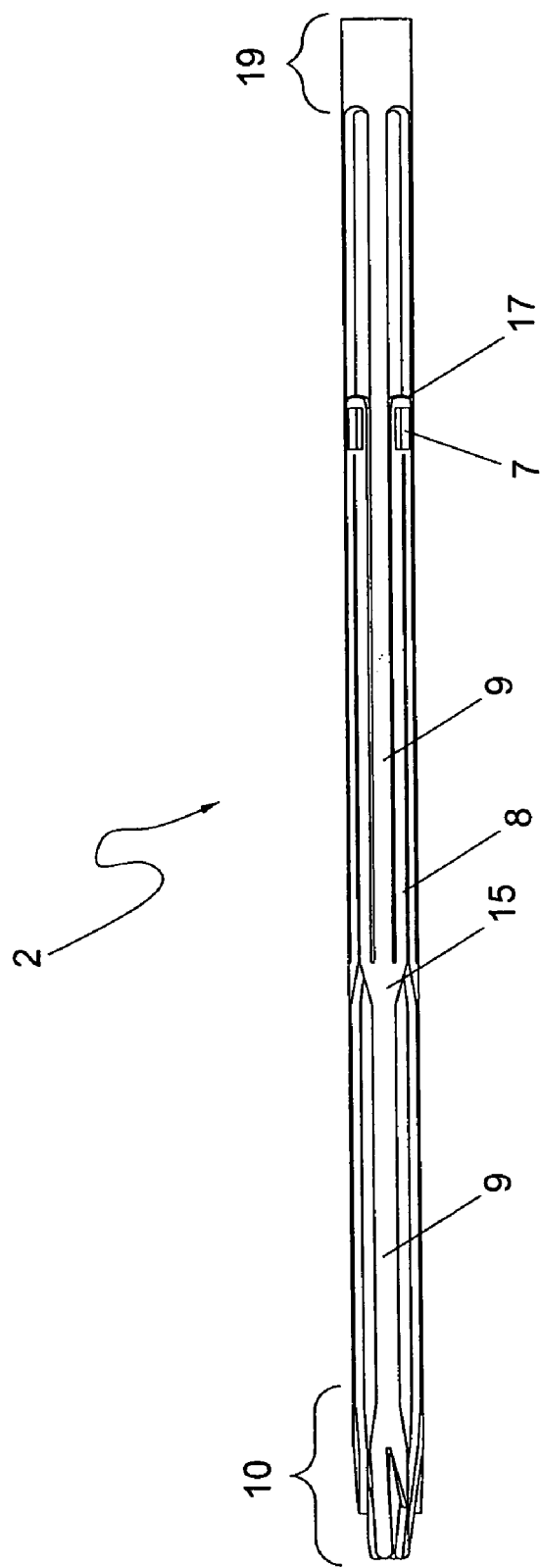
FIG. 5 is a plan view of the filter cone/centering strut subassembly 2 of the vena cava filter device of the current invention in a non-expanded state.
Figure 7:
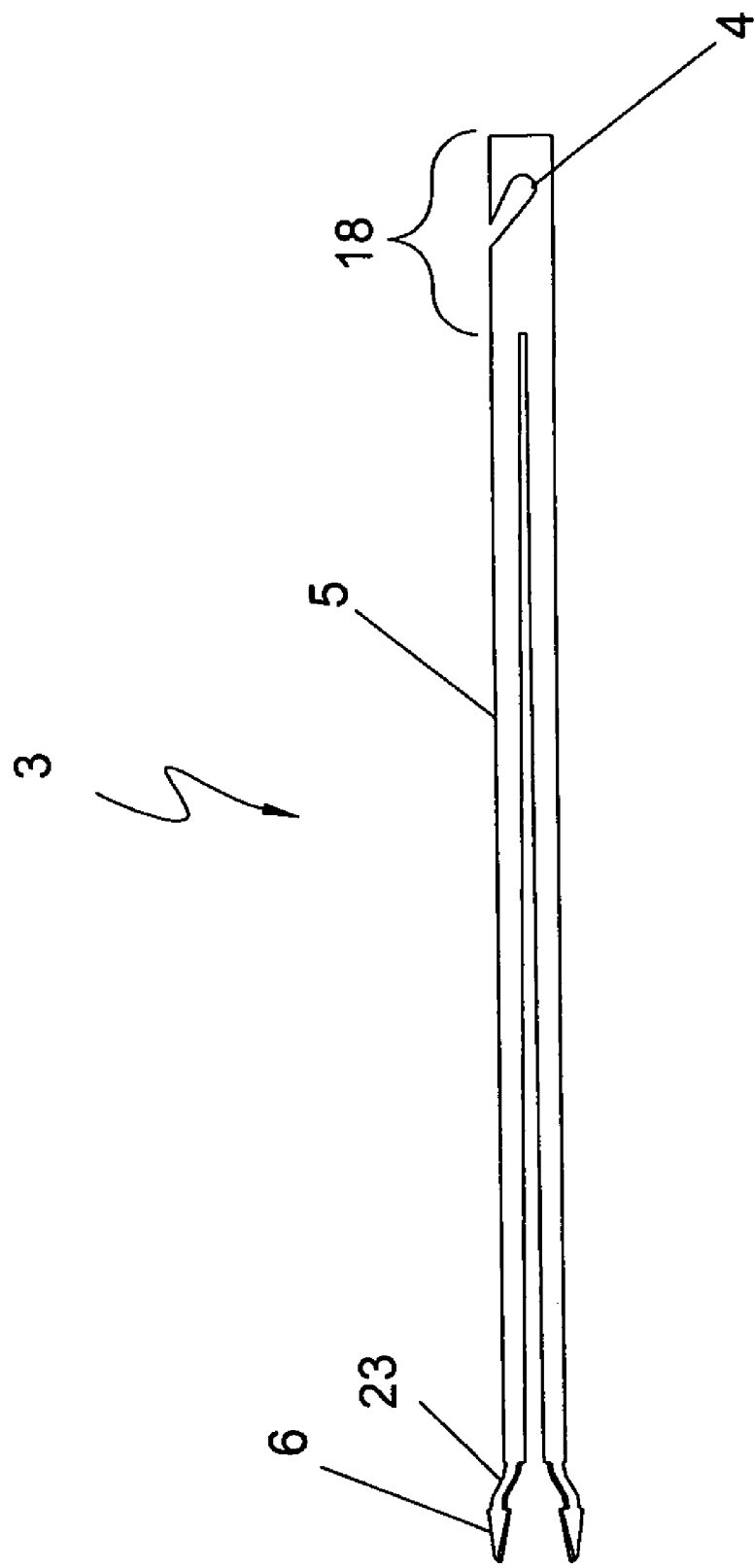
FIG. 7 is a plan view of the control/connector strut subassembly 3 of the vena cava filter device.

To manufacture the device, the tube subassemblies are first cut into the desired configuration using laser-machining techniques commonly known in the art. Other cutting techniques such as photo or acid etching may be used to form the desired cut patterns for subassembly 2 and subassembly 3. Material is cut away from each tube in a pre-determined pattern to form the desired configuration, as shown in FIG. 5 and FIG. 7. The outer cut tube is then annealed or heat-treated to form the expanded deployment shape of FIG. 3A. The barb portion of second inner tube 3 may also be annealed into a curved configuration. To assemble the filter, the inner cannula 37 is placed within the lumen of subassembly 2 and abuts up against the upstream edge of a hub/non-slotted section 18. The cannula 37 may either be press fit or connected in other ways commonly known in the art. The two tube subassemblies 2 and 3 are then coaxially assembled together and then constrained within a sheath or catheter to the non-expanded profile as shown in FIG. 1.

In one novel aspect of the invention, the method of manufacture of each tube subassembly 2 and 3, and cannula 37, provides unitary components that have no welded joints. The singular tube construction of each subassembly avoids the necessity of welding or otherwise connecting individual wire elements. In addition, the assembly of the tubular subassemblies 2 and 3, and the inner cannula 37 into the final finished vena cava filter device 1 may be achieved without requiring any welding steps.

As is well known in the art, welding or otherwise connecting shape-memory materials is difficult, time-consuming and results in connection points that are more susceptible to long-term fatigue stress and loss of structural integrity than non-jointed segments. By contrast, the lack of weld joints in the present invention: (1) minimizes the possible complication of filter fracture caused from the loss of structural integrity of the filter over time; (2) simplifies assembly whereby decreasing manufacturing costs; and (3) provides a lower unexpanded profile of the filter allowing the use of smaller delivery and retrieval systems.

Figure 2:
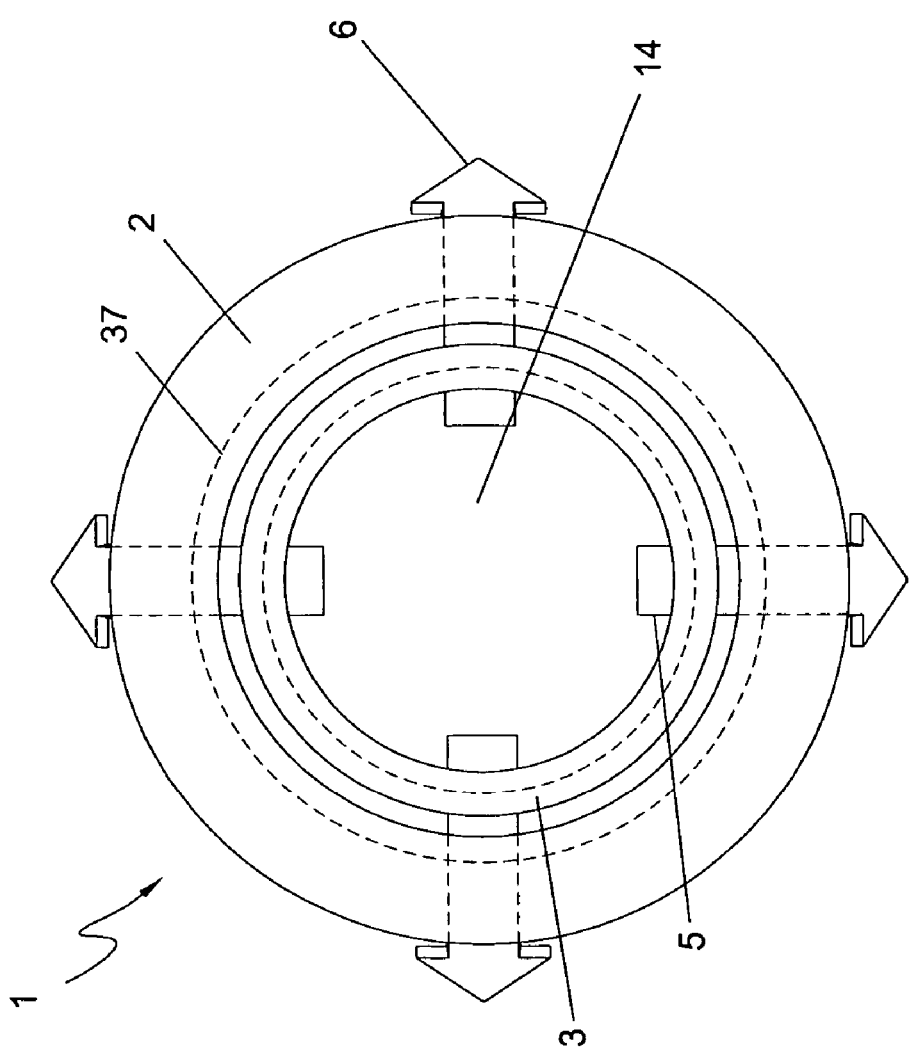
FIG. 2 is an enlarged end view of the vena cava filter device of FIG. 1. Hidden lines have been removed for clarity.

FIG. 2 is an enlarged end view from the downstream end of the vena cava filter 1 depicted in FIG. 1 in a collapsed state. The filter cone/alignment strut subassembly 2 coaxially surrounds the control strut subassembly 3. The outer diameter of the subassembly 2 is preferably 0.071"0 for use with a small delivery sheath such as a 6 French size. The inner diameter of the filter cone/alignment strut subassembly 2 is approximately 0.051", providing a wall thickness of approximately 0.010". The inner wall of the control strut subassembly 3 defines a through channel 14 which is dimensioned at approximately 0.038" to allow the passage of a 0.035" guidewire or other device (not shown) through the filter 1 to facilitate deployment or removal from the vena cava.

The outside diameter of the control strut subassembly 3 is preferably 0.048" with a corresponding wall thickness of 0.005". Although barbs 6 which extend primarily in a radial direction which is perpendicular to the plane of FIG. 2, they also extend beyond the longitudinal profile of the filter cone/centering strut subassembly 2 by approximately 1 millimeter when assembled. When constrained within the delivery catheter or sheath, the barbs 6 are forced down onto and become aligned with the outer surface of the filter cone/centering strut subassembly 2. Other alignment strut subassembly 2 and control strut subassembly 3 dimensions are possible.

The outside diameter of the cannula 37 is preferably 0.053" with a corresponding inner diameter of 0.041". Cannula 37 terminates at upstream cannula end 38 and downstream cannula end 39 (see FIG. 3D), with a length of approximately 0.13". Downstream cannula end 39 is sized to be friction fit into the inner diameter of the non-slotted section 19 of the filter cone/alignment strut subassembly. The lumen of the inner cannula 37 accepts control struts/arms 5 as shown in FIG. 2. As stated, subassembly 3, is cut from a cannula with an outside diameter of 0.048". This creates an interference fit with the inside diameter of cannula 37. The slots cut in subassembly 3 allow the control struts 5 to compress centrally and pass through cannula 37.

Figure 3B:
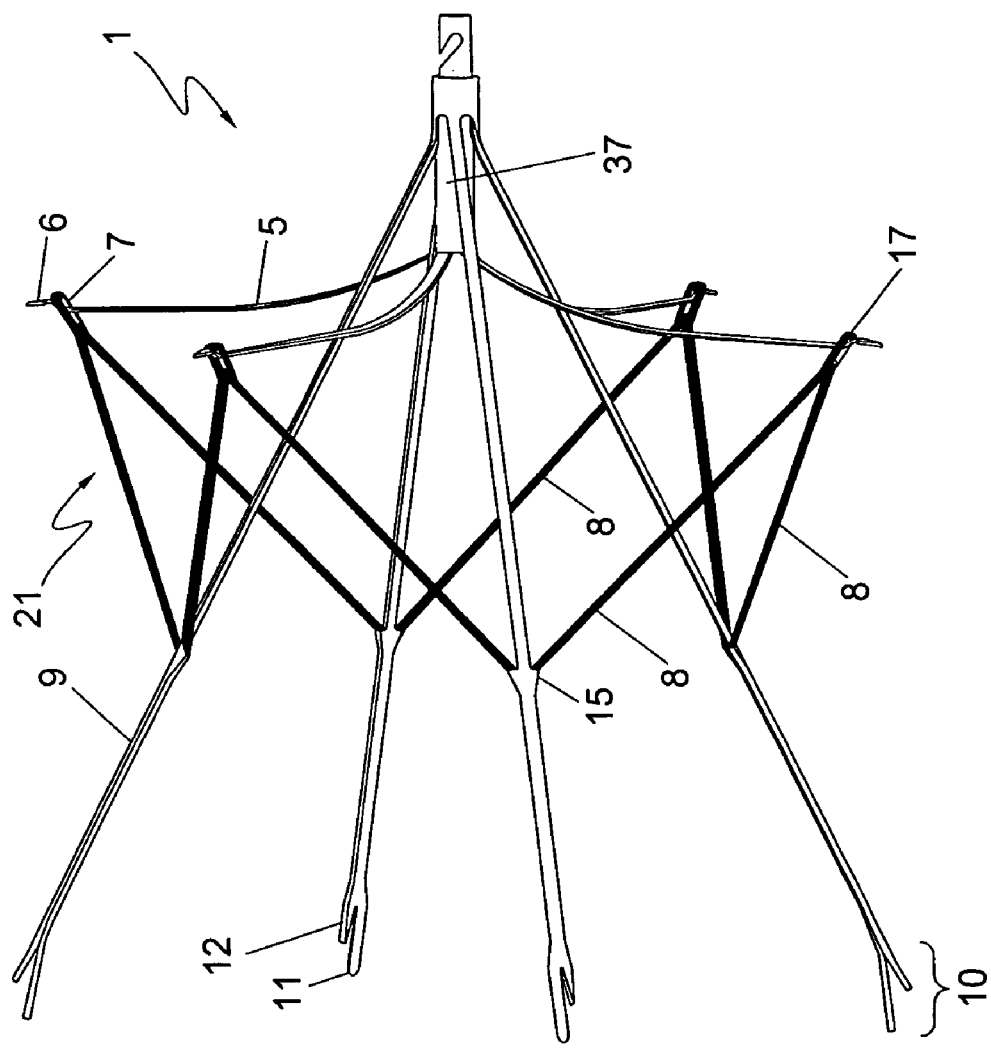
Figure 3C:
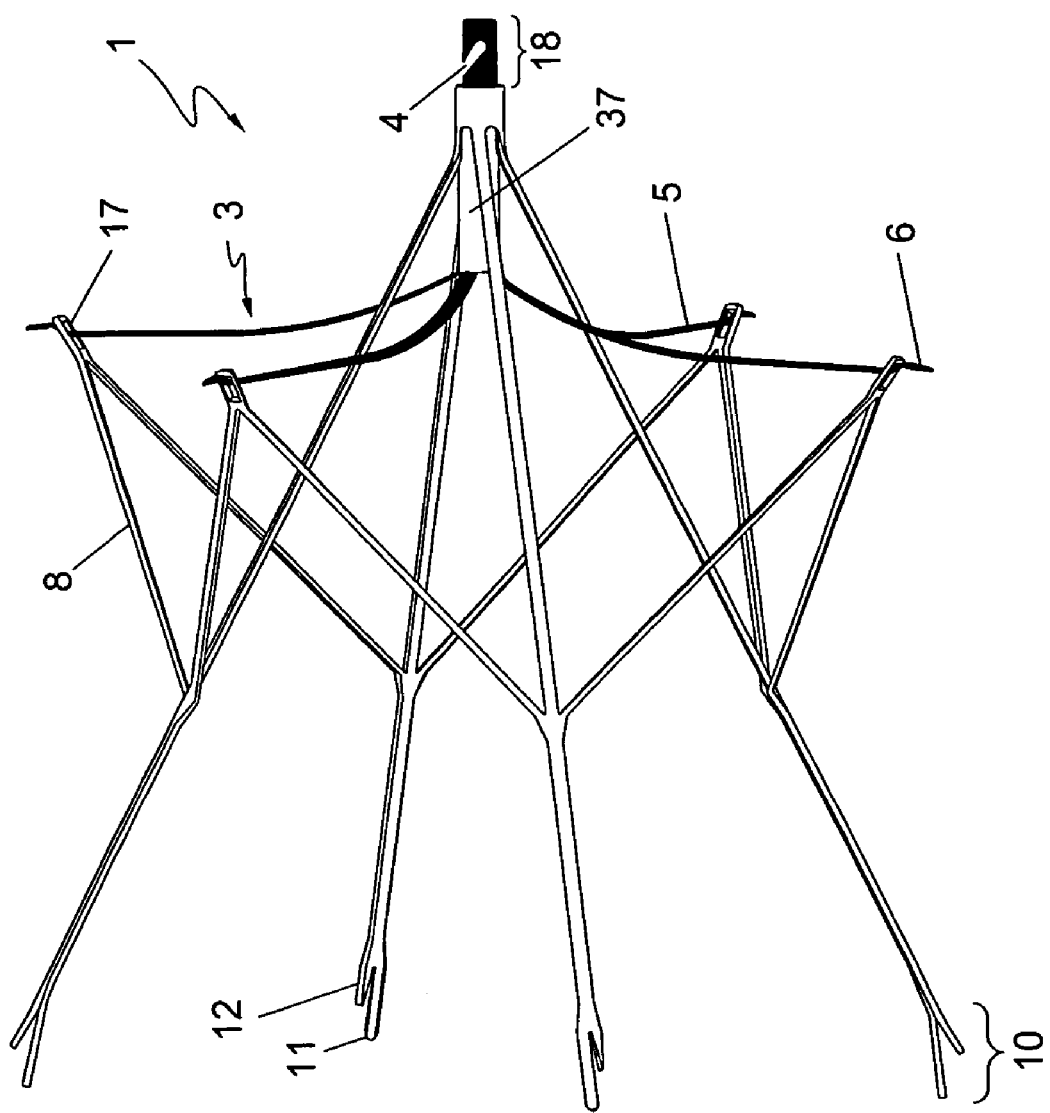

Referring now to FIG. 3A through FIG. 3C, plan views of the device 1 of the current invention are depicted in an expanded shape highlighting different functional components. FIG. 3A highlights the conical filtering configuration/section 20 (bolded for clarity) of the filter cone/alignment strut subassembly 2. The conical filtering configuration 20 performs the primary clot capturing and lysing function of the device as well as a secondary anchoring function to prevent migration of the filter in an upstream or retrograde direction. The configuration 20 is comprised of individual filtering struts/legs 9 and a hub 19 which is a non-slotted tubular section. Each filtering leg 9 extends radially and outwardly in an upstream direction from the hub 19 of the outer tube. In the preferred embodiment, the filtering legs 9 are four in number, although other configurations are possible. Leg 9 terminates in a wall-engaging portion 10.

In the embodiment shown, the device 1 contacts the vessel wall on a first plane at apices 17 which are the downstream ends of the alignment struts 8 as shown in FIG. 3B and on a second more upstream plane at wall-engaging portion 10 of the filter legs 9 which are the upstream ends of the filter legs. The wall-engaging portion 10 of leg 9 is approximately 2 to 5 mm in length and is comprised of a foot 11 and barb 12. The barb 12 functions to positively anchor the legs 9 in the vena cava wall to prevent retrograde migration of the device. The barbs are dimensioned at about 0.5 to 1.5 mm in length to ensure stable securement to the wall without migration of the legs 9 through the vena cava into the surrounding tissue. The angle of the barb relative to the longitudinal axis of the device is between 15 and 40 degrees, allowing for disengagement during retrieval in a direction that minimizes tearing of the vessel wall. The foot 11 rests parallel to and on the surface of the vessel wall, providing a platform that limits the depth of barb 12 penetration during implantation.

FIG. 3B highlights the alignment structure/section 21 (bolded for clarity) of the filter 1. Although highlighted separately in FIG. 3A and FIG. 3B for clarity purposes, the alignment structure 21 and conical filter 20 are formed of a single tube 2 with no welded connection points. The alignment structure 21 provides central alignment of the conical filter 20 within the vessel and ensures symmetrical deployment of the filter legs 9. The alignment structure 21 shown in FIG. 3B is formed of a series of individual alignment struts 8. In the preferred embodiment, the alignment struts 8 are eight in number, although the number of struts 8 is dependent on the number of filtering legs 9. Each strut 8 is approximately 0.014" wide with a thickness of 0.010" corresponding to the wall of the outer tube subassembly 2.

Each alignment strut 8 terminates at a downstream apex 17 which contains a barb-receiving hole 7, which accepts barb 6 of control strut 5. The other end of each alignment strut 8 connects to the leg 9 at a juncture/connecting point 15. The juncture as shown is at an intermediate zone, preferably a mid-zone, which is located away from the upstream end 10 and the hub/downstream end 19. The downstream apex 17 of each alignment strut 8 forms a juncture with the downstream end of an adjacent alignment strut. The series of alignment struts 8 together form an alignment structure 21 which when expanded angles radially and outwardly from the longitudinal axis of the filter in a downstream direction at an angle to contact the vessel wall at apex 17. Thus, in one novel aspect of the invention, centering of the filtering legs 9 within in the vessel is achieved with only point contact to the vessel wall and without extending the overall length of the device 1.

The interconnecting arrangement of the alignment struts 8 to each other ensures that each strut and filter leg 9 are symmetrically deployed around the inner vessel wall. Leg crossing or entanglement during or after deployment is avoided by the interconnecting design of the alignment struts 8, which ensure equal spacing is maintained between each apex at both the upstream and downstream ends of the filter. The symmetrical deployment, anchoring and alignment features of this design allow the filter to be consistently placed in vena cavas of varying dimensions and shapes.

FIG. 3C highlights control strut subassembly 3 (bolded for clarity), which is formed from the inner tube 3. The control strut subassembly 3 functions to control deployment of the device, maintain central alignment during implantation, provide a secondary filtering mechanism and facilitate the collapse of the device 1 during retrieval. The control strut subassembly 3 is comprised of a series of individual control/connector struts 5 connected to a hub which is a non-slotted section 18 at the downstream end and terminating in barbs 6 at the other end. The non-slotted section 18 of the control strut subassembly 3 is approximately 0.50" in length. Within the non-slotted section 18 is a retrieval hook 4 for the capture and removal of the device from the vena cava. The struts are preferably 25 to 31 mm in length to accommodate a wide range of vena cava sizes.

In an alternative embodiment, the width of each control arm 5 tapers from about 0.010" wide at the non-slotted section 18 to approximately 0.024" at the downstream apex 17. This design is advantageous in that the struts have a reduced profile at the center of the vessel to minimize blood flow turbulence with increased width, strength and stiffness at the anchoring portion of the strut 5 for secure attachment and fatigue resistance as the vessel wall moves.

When fully deployed, the control struts 5 are drawn outwardly from the non-slotted section 18 at an angle of almost 90 degrees relative to the longitudinal axis of the vessel. The control struts 5 bisect the cross-sectional area between two adjacent filter legs 9 providing a secondary level of cava filtration (see FIG. 4). The drawn out control struts 5 provide a secondary filtering mechanism by capturing thrombus that might otherwise pass through the area between two adjacent filtering legs 9.

The barbs 6 are moveably connected to apices 17 of the alignment struts 8 through the barb-receiving holes 7. The barbs 6 penetrate the vessel wall at an angle substantially perpendicular to the vessel wall. This angle is advantageous when the filter is removed because the barbs will pull out of the wall in a manner that creates only minimal vessel wall damage rather than slicing or tearing the neointimal layer. Other barb configurations are also possible, including barbs of differing profiles and locations along the alignment struts 8.

FIG. 3D illustrates the inner cannula/tube 37 component of filter 1 and its position within the assembled filter. Similar to the other subassemblies, the cannula 37 is formed from a single tube with no welded connections. The inner cannula 37 is not laser cut, although the upstream cannula end 38 is preferably radiused to facilitate smooth deployment and retraction of the control struts 5. The cannula 37 is positioned coaxially between the non-slotted section 18 of the control strut subassembly 3 and the non-slotted section 19 of the outer tube 2, press fit into assembly 2 and slidable with assembly 3. Thus positioned, the inner cannula 37 functions to facilitate retrieval by directing the collapsing force of the alignment struts 8 inwardly instead of longitudinally. The inner edge 38 of the cannula 37 is chamfered to further facilitate retraction of the control struts 5 during retrieval.

Figure 3E:
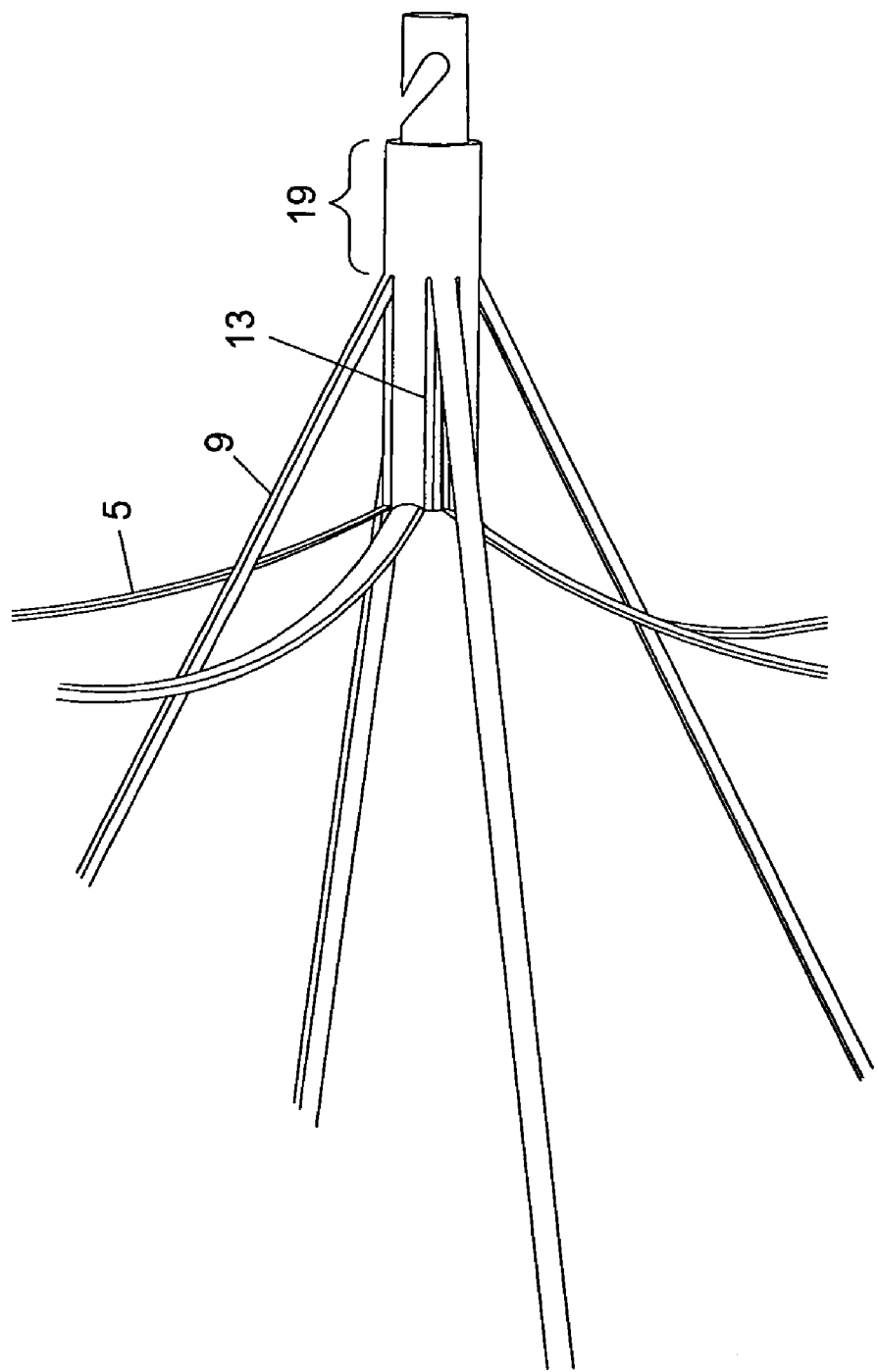
FIG. 3E is an enlarged partial plan view of the vena cava filter device in an expanded position showing an alternative embodiment using extensions 13.

FIG. 3E illustrates an alternative design for directing the expansion and collapsing force of the alignment struts which does not require a separate inner cannula component. The filter cone/alignment strut subassembly 2 is cut in a pattern that includes the filter legs 9 and extensions 13. Extensions 13 are arranged between each filter leg 9 and act to direct the expansion of the control struts 8 outwardly in a controlled manner during deployment and inwardly during retrieval. The inner upstream edge of extension 13 may be beveled to facilitate smooth expansion and retrieval of the filter.

Figure 4:
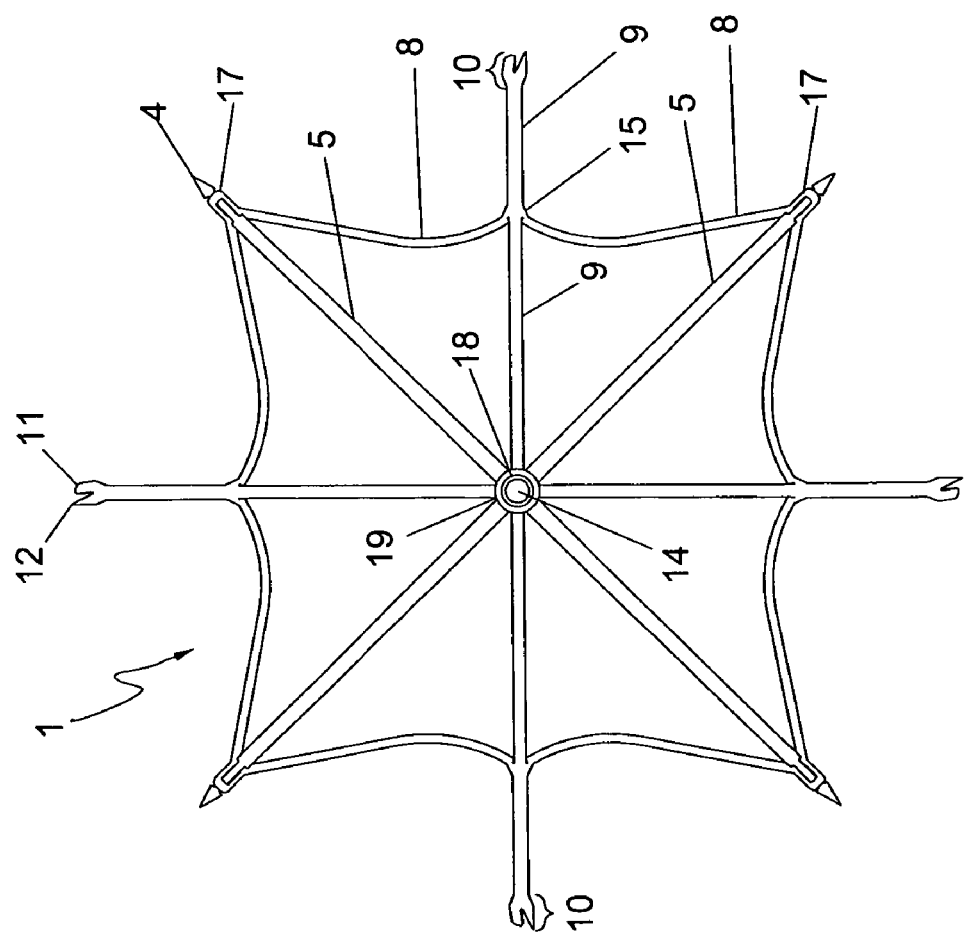
FIG. 4 is an end view of the expanded vena cava filter as depicted in FIGS. 3A-3C.

Referring now to FIG. 4, an end view of the filter device 1 in an assembled and expanded state is shown from a downstream view. The alignment struts 8 self-center the device 1. Primary filtering legs 9 extend radially outward from the non-slotted outer tube section 19. The alignment struts 8 intersect filtering legs 9 at connecting point 15 and act to prevent the legs from crossing each other during deployment and implantation. The control struts 5 bisect the cross-sectional area between two adjacent filter legs 9 providing a secondary level of cava filtration. Thus, control struts 5 provide a secondary filtering mechanism by capturing thrombus that might otherwise pass through the area between two adjacent filtering legs 9. The control struts 5 extend outward from the non-slotted section 18 through the end of cannula 37 (not shown). Barbs 6 at apexes 17 provide primary fixation against downstream migration. Wall-engaging portion 10, comprised of barb 12 and foot 11, provides a secondary fixation against upstream migration of the device 1. The through channel 14 provides a lumen through which a guidewire or other medical device accessories can be advanced to assist in placement or retrieval.

Figure 6:
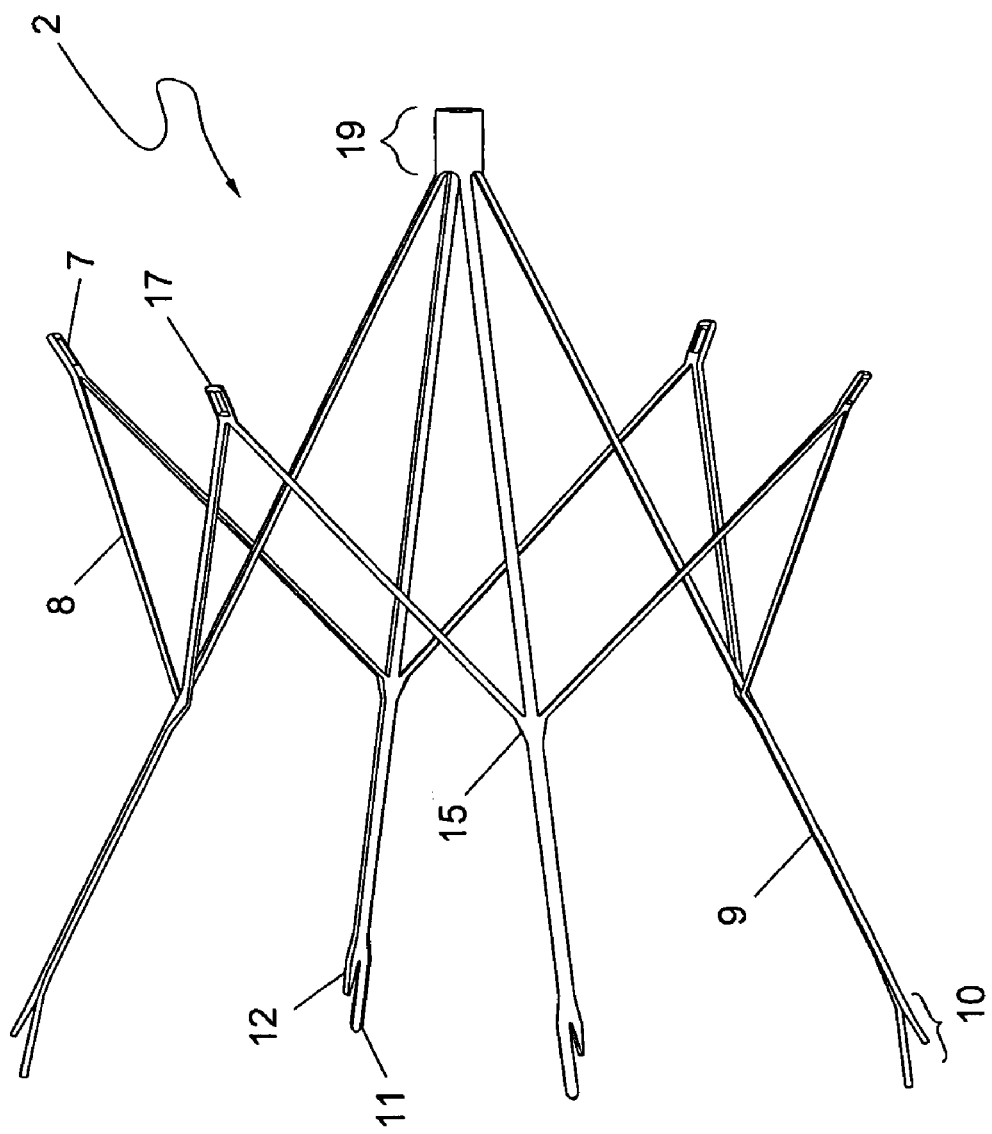
FIG. 6 is a plan view of the filter cone/centering strut subassembly 2 of a retrievable vena cava filter device in an expanded state.

Turning now to a detailed description of filter cone/alignment strut subassembly 2, plan views of the subassembly are shown in a non-expanded and expanded state in FIG. 5 and FIG. 6 respectively. FIG. 5 illustrates the preferred pattern to which the tube is laser-cut to form the non-slotted hub section 19, alignment struts 8, filtering cone legs 9, downstream apices 17, barb-receiving hole 7, and the wall engaging portion 10 of filtering legs 9 which comprise the filter cone/alignment strut subassembly 2.

After subassembly 2 is laser cut into the pattern shown in FIG. 5, it is annealed into the expanded shape shown in FIG. 6. When expanded, the interconnecting alignment struts 8 provide superior centering of the conical shape within the vessel. Centering is achieved by providing two sets of point contact with the vessel wall along two separated planes. Specifically, each alignment strut 8 contacts with the vessel wall at the apex 17, providing a first downstream plane of contact. The wall-engaging portion (upstream end) 10 of the conical filtering legs 9 contact the vessel wall at a second upstream plane. Thus, the filter legs/struts 9 and alignment struts 8 together function to provide a stable, self-centering device with minimal vessel wall contact.

Thus, another advantage of the current device 1 is that the filter is deployed symmetrically within the vessel. Problems with tilting, leg-crossing and asymmetrical axial alignment of struts are eliminated by the interconnecting strut design. Each strut 8, because it is connected at the apex 17 to the adjacent strut 8, will automatically align symmetrically against the vessel wall, regardless of the individual anatomical profile of the vessel. The legs 9 also deploy symmetrically due to the interconnections of the struts 8.

The wall-engaging portion 10 of the conical filtering legs 9 provide vessel wall fixation to prevent migration of the device 1 in a upstream direction. Wall-engaging portion 10 is comprised of a foot 11 and a barb 12. Barb 12 engages the vessel wall and is dimensioned to ensure optimum penetration depth. Foot 11 rests against the vessel wall in a longitudinal direction and prevents over penetration of barb 12. It is well known in the art that endothelialization of any portion of a filter strut in contact with the vessel wall occurs as early as twelve days after filter placement. The wall-engaging portions 10 of the legs 9 and apices 17 of the alignment struts provide secure engagement with only minimal contact with the vessel wall, thereby reducing the extent of endothelialization at the device site. Thus, this design facilities retrieval because the wall-engaging portions will disengage from the vessel wall without significantly disrupting the endothelial layer of the vessel wall.

Thus, the filter cone/centering strut subassembly 2 incorporates a stabilizing structure that ensures the centering alignment of the conical filter 20 is maintained throughout the implantation period of the device. This unique design overcomes prior art problems with cone misalignment and tilting and reduces the resulting complications of blood flow turbulence, compromised lysing capability and filter-induced thrombus buildup. The overlapping design of the alignment struts 8 and filter legs 9 represents another advantageous aspect of the current invention. This overlapping design minimizes the overall length of the device when deployed, provide optimal filtering angle and also provides a mechanism for accurate, reliable and easy placement during deployment.

Turning now to the control strut subassembly 3, a plan view of the subassembly is shown in FIG. 7. FIG. 7 illustrates the preferred pattern to which the tube is laser-cut to form the control struts 5 which terminate at the upstream end in barbs 6 and the downstream end with the non-slotted section 18 of the control strut subassembly 3. The non-slotted section 18 includes a cut out section that forms the retrieval hook 4. Each strut includes a curved transition segment 23 of reduced width between the straight portions of control strut 5 and barb 6.

Prior to assembly with the filtering cone/alignment strut subassembly 2 and inner cannula 37, the series of control struts 5 are substantially straight and uncurved. Only the curved transition segment 23 portion of the control struts is pre-shaped using standard nitinol heat forming processes. When barb 6 of control strut 5 is assembled through the barb receiving hole 7 of downstream apex 17 and subassembly 2 is allowed to expand, the interlocking connection of the two components at apex 17 draws the control struts 5 outwardly from the non-slotted section 18 curving to a generally perpendicular orientation relative to the vessel wall.

Figure 8:
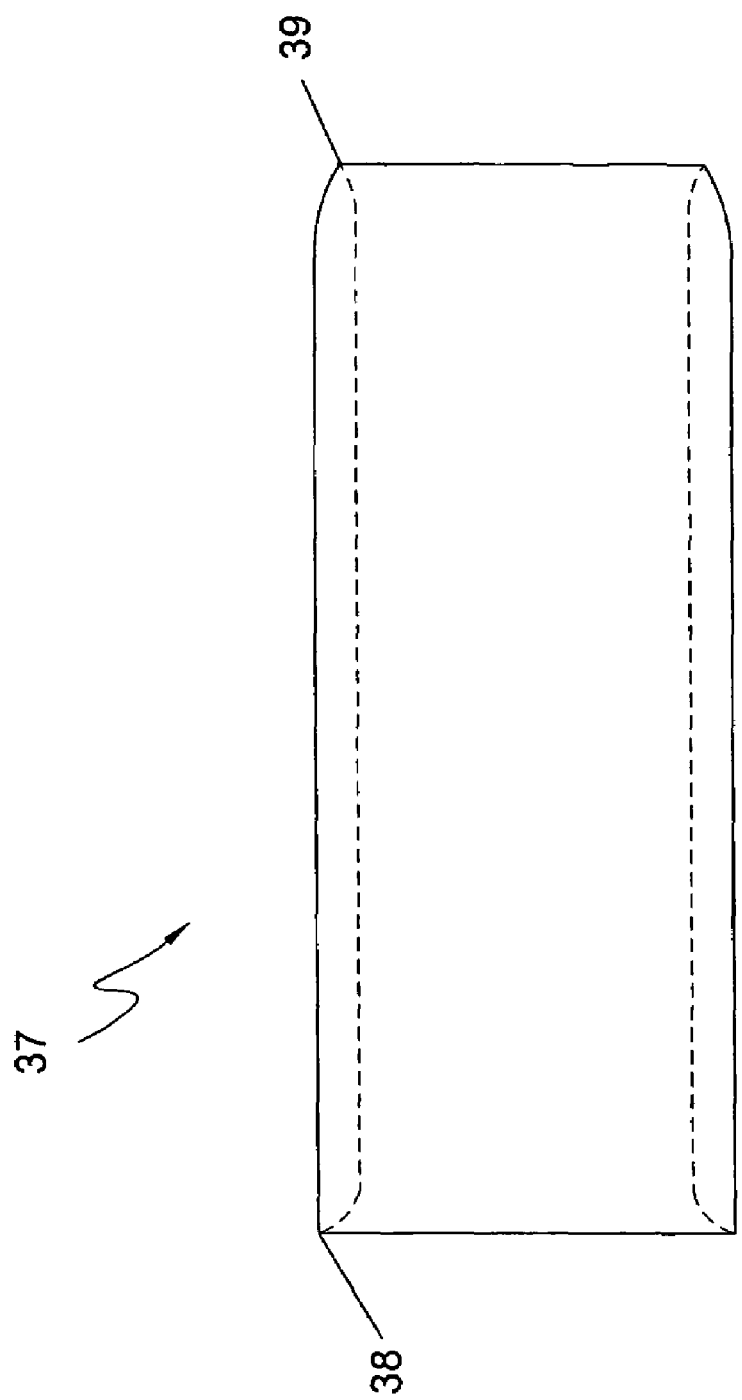
FIG. 8 is an enlarged plan view of the inner cannula 37 of the vena cava filter device.

Referring now to FIG. 8, a plan view of the inner cannula 37 component of the filter device 1 is shown. Inner cannula 37 is formed of a metallic material and terminates in cannula end 38 at the upstream end and cannula end 39 at the downstream end. Cannula end 38 may include an internal bevel or chamfer which provides a smooth, curved inner surface to facilitate the expansion and retraction of the control struts 8 during deployment and retrieval. Cannula end 39 includes an external bevel or chamfer which facilitates the insertion of the cannula 37 into the inner diameter of non-slotted section 19 of outer tubular subassembly 2 during the assembly.

Figure 9:
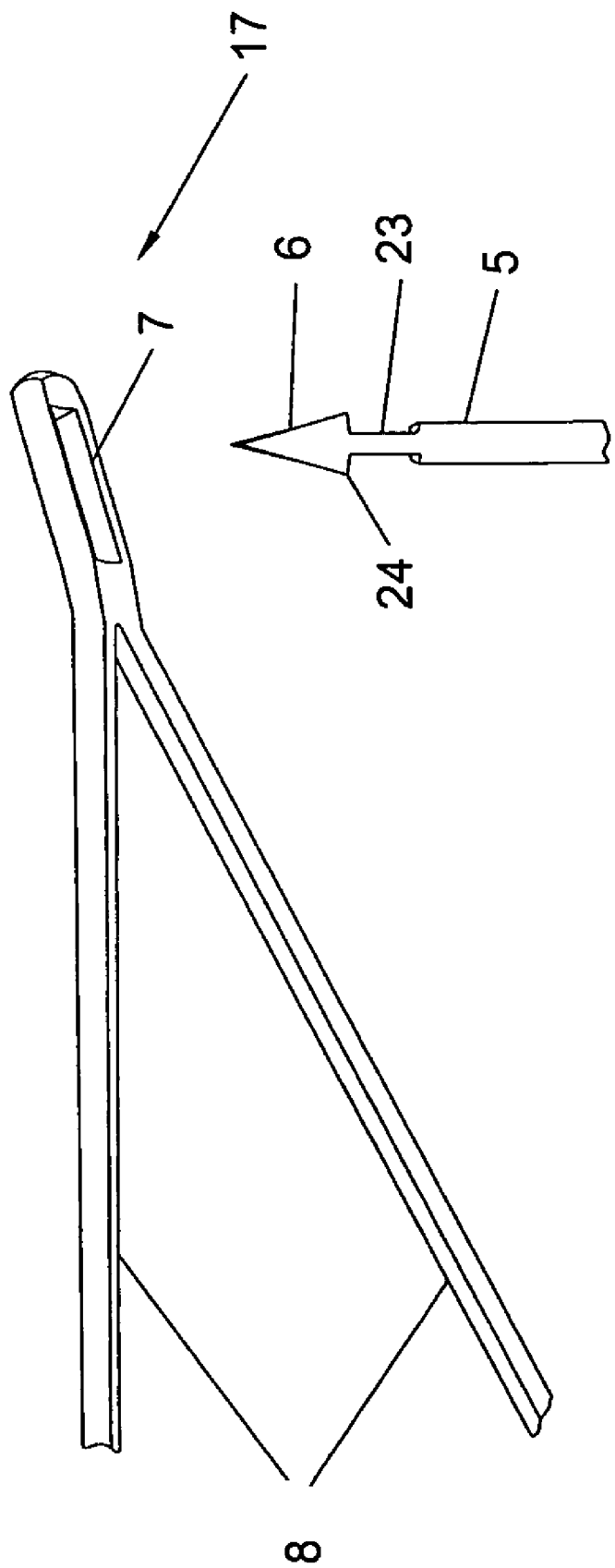
FIG. 9 is an enlarged plan view of the downstream apex of the alignment strut with a control strut as it is being inserted into the receiving hole.

Referring now to FIG. 9, an enlarged plan view of the downstream apex 17 of the alignment strut 8 is shown with an end portion of the unassembled control strut 5. The downstream apex 17 contains a barb-receiving hole 7 through which the barb 6, located at the end of control strut 5, is received. The barb-receiving hole 7 is sized to pass barb 6 when oriented in one direction, allows rotation during assembly and prevents disconnection when the barb 6 is oriented 90 degrees in the other direction.

In the preferred embodiment, the barb-receiving hole 7 has a longitudinal slot length of approximately 0.016" for slideably accepting the barb 6, which has a base 24, of approximately 0.015" in width. The barb-receiving hole 7 is dimensioned with a slot width of approximately 0.008" so as to accept the barb thickness of 0.005". The control strut 5 width is approximately 0.010" with segment 23 having a reduced width of approximately 0.005" to allow rotation within the barb-receiving hole 7. Curved segment 23 also functions to limit movement of the control strut 5 once positioned within the slot to the length of the reduced dimension segment 23. In addition, segment 23 is designed to achieve a lower overall profile when in the constrained, undeployed position, thus allowing use of a smaller device delivery system.

The barb 6 end of the control strut 5 is pre-shaped to the engaged orientation such that the barb base 24 abuts the lateral sides of the hole 7. When assembling the control strut subassembly 3 with the filtering cone/alignment strut subassembly 2, barb 6 is oriented to allow passage through the barb-receiving hole 7. Once threaded through the barb-receiving hole 7, the barb 6 will be returned to its preformed orientation by turning 90 degrees. In this position, the barb 6 dimensions are wider than the barb-receiving hole 7 and accordingly it cannot slide back through the barb-receiving hole 7.

Figure 10A:
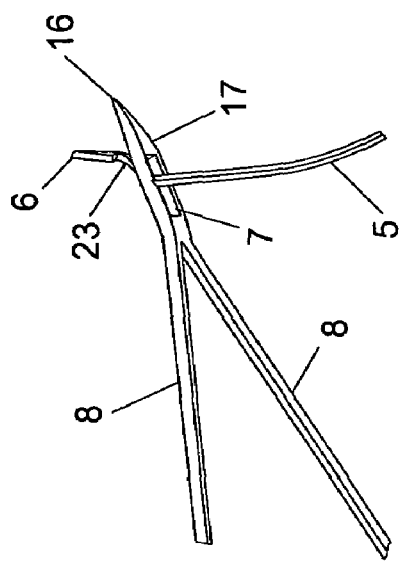
FIG. 10A is an enlarged plan view of the downstream apex of the alignment strut assembled with the control strut in an expanded position.

When the device is assembled with the control strut subassembly 3, the barb 6 and the end section of the control strut 5 extend through the barb-receiving hole 7. FIG. 10A illustrates the relationship between the control strut 5 with barb 6 and the downstream apex 17 with barb receiving hole 7 when deployed within the vena cava. Barb 6 embeds into the vessel wall, providing a securement mechanism to prevent migration of the filter 1. Specifically, the control strut 5 orientation of the barb 6 is perpendicular to the vessel wall and blood flow and thus provide increased resistance to filter movement when under clot load. As will be discussed in further detail below, the control arm/barb orientation is in line with the withdrawal direction and thus allows the barbs to pull straight out of the vessel wall whereby minimizing wall damage during retrieval.

Figure 10B:
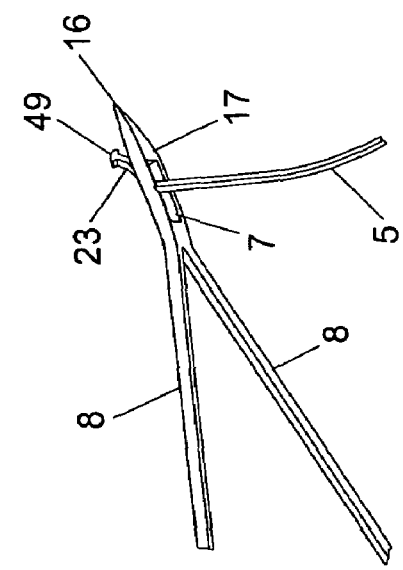
FIG. 10B is an enlarged plan view of the downstream apex of the vena cava filter depicting alternative configuration of the anchoring mechanism.
Figure 10C:
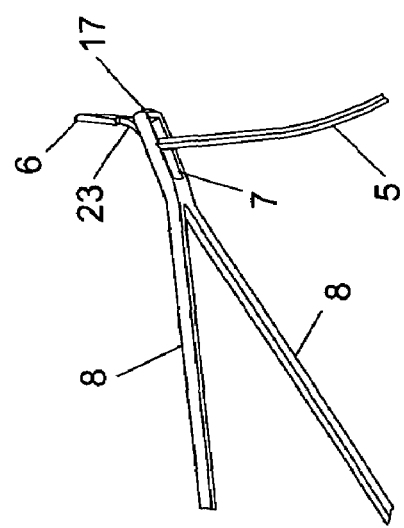
FIG. 10C is an enlarged plan view of the downstream apex of the vena cava filter depicting a further alternative configuration of the anchoring mechanism.

Alternative embodiments of the wall-engaging portion of the control arm 5 and downstream apex 17 is shown in FIG. 10B and FIG. 10C. The barb-receiving hole 7 has a longitudinal slot length of approximately 0.016" for slideably accepting the button end 49, which has a barbless curved outer profile. Fixation is provided by the downstream apex 17 terminating in a barb 16 which penetrates the vessel wall at a downstream angle. The barb orientation relative to the vessel wall prevents downstream migration, even under heavy clot load. Specifically, increased force against the filter caused by captured thrombus will produce and increase the force against the barbs, driving them deeper into the vessel wall. The depth of penetration is limited by the length of control strut 5 which prevents barb portion 16 of apex 17 from driving too far into the vessel.

FIG. 10C depicts a wall-engaging portion of the filter in which anchoring barbs are present at the termination of both the apex 17 and the control strut 5. The interconnecting arrangement of the control strut 5 and the apex 17 together limit the depth of penetration. The advantage of this embodiment is superior fixation from a dual-anchoring system where the clot load against the filter is the heaviest. In all three embodiments, the design limits the amount of penetration by the barbs.

Figure 11A:
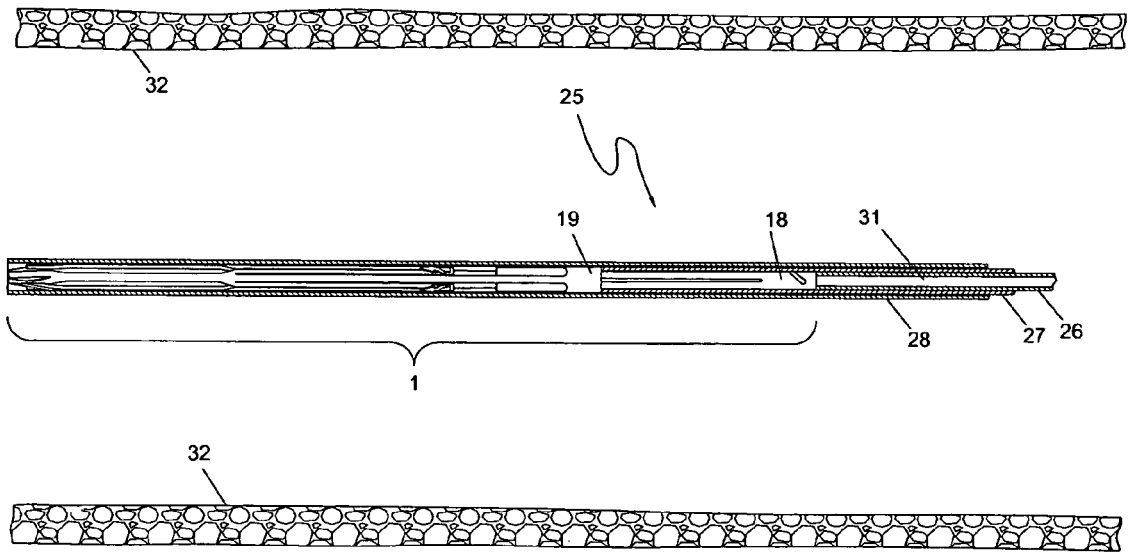
FIGS. 11A through 11D illustrate a method of deploying the vena cava filter within the vessel.

The method of filter deployment will now be described with reference to FIGS. 11A-11D. For the purposes of clarity, FIGS. 11A-11D depict the filter in a slightly different rotation than FIGS. 3A-3D. To place the filter percutaneously, a deployment device 25 containing the filter 1 in a collapsed state is introduced through a standard introducer sheath (not shown) through the jugular vein into the vena cava 32. FIG. 11A depicts the filter 1 collapsed within the deployment device 25 prior to deployment. The deployment device 25 is preferably a three-component coaxial tube system comprising an inner deployment member 26, intermediate deployment member 27 and outer deployment tube 28.

The outer deployment tube 28 coaxially surrounds the intermediate member 27. Outer deployment tube 28 provides an outer housing to retain the filter 1 in a constrained/collapsed position prior to deployment and also functions to deploy the filter legs 9 when the outer tube 28 is retracted.

Intermediate member 27 abuts up against and is releaseably connected to the non-slotted section 19 of the filter cone/alignment strut subassembly. Member 27 may be in a coaxial arrangement with inner member 26 or may be longitudinally juxtaposed with inner member 26 within the outer deployment tube 28. Member 27 functions to prevent filter 1 from moving in a longitudinal direction within the deployment device 25, when the outer tube 28 is retracted or advanced.

The inner deployment member 26 controls the deployment and retraction of the control struts 5 and the interconnected alignment struts 8. Inner member 26 may include a through lumen 31 for guidewire passage. Inner member 26 abuts up against and is releaseably connected to the non-slotted section 18 of the control strut assembly 3. Advancement of member 26 forces the control strut assembly forward into an expanded state.

The tubular construction of the filter 1 minimizes the deployment device 25 diameter. In the preferred embodiment, the deployment device 25 will fit within a 6 French delivery system, providing a small insertion site and less trauma to the patient.

Once correct positioning within the vena cava has been confirmed, the filter 1 is controllably deployed in the vessel 32. In one embodiment, the filter 1 is deployed through a series of three steps. Each step controls the deployment of a separate part of the filter. In this staged deployment, the filter legs 9 are first released, followed by release and expansion of the alignment 8 and control struts 5. After the filter is fully expanded and engaging the vessel on two planes, a third step separates the deployment system 25 from the filter 1. The three steps are sequentially performed in a smooth motion.

Figure 11B:
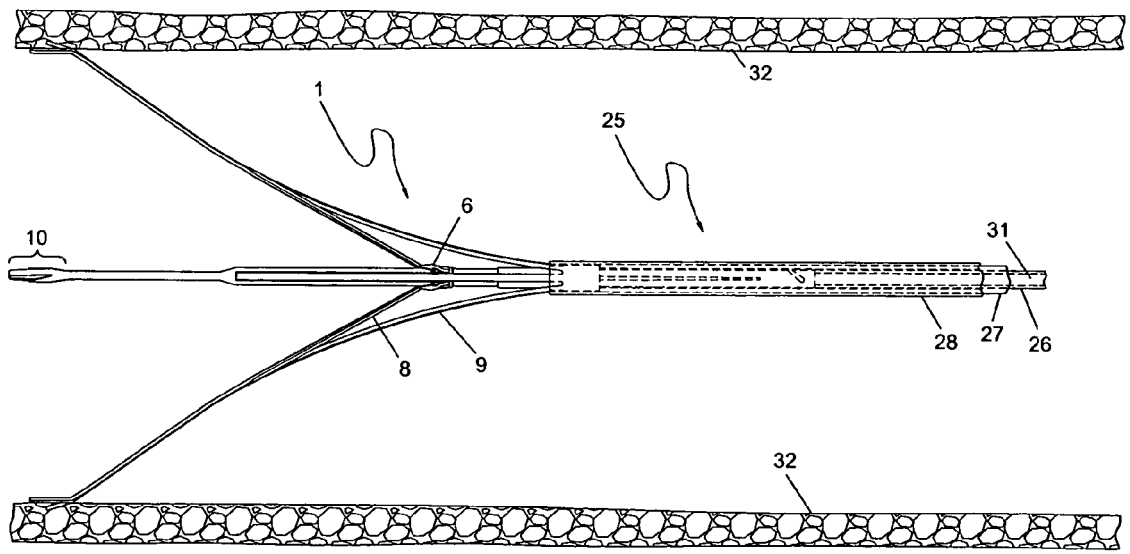

FIG. 11B illustrates the first deployment step in which the filter legs 9 are deployed. The outer deployment tube 28 is retracted while maintaining the position of the inner member 26 and intermediate member 27. As the outer tube 28 is retracted, the upstream section of the filter 1 is uncovered and expands to its pre-formed shape, causing the filter legs 9 to engage the vena cava wall 32. Specifically, barbs 12 of the wall-engaging portion 10 of the filter legs 9 will contact and advance into the vessel wall 32. Advancement of the barbs 12 is stopped when the foot 11 contacts the surface of the vessel wall 32.

Figure 11C:
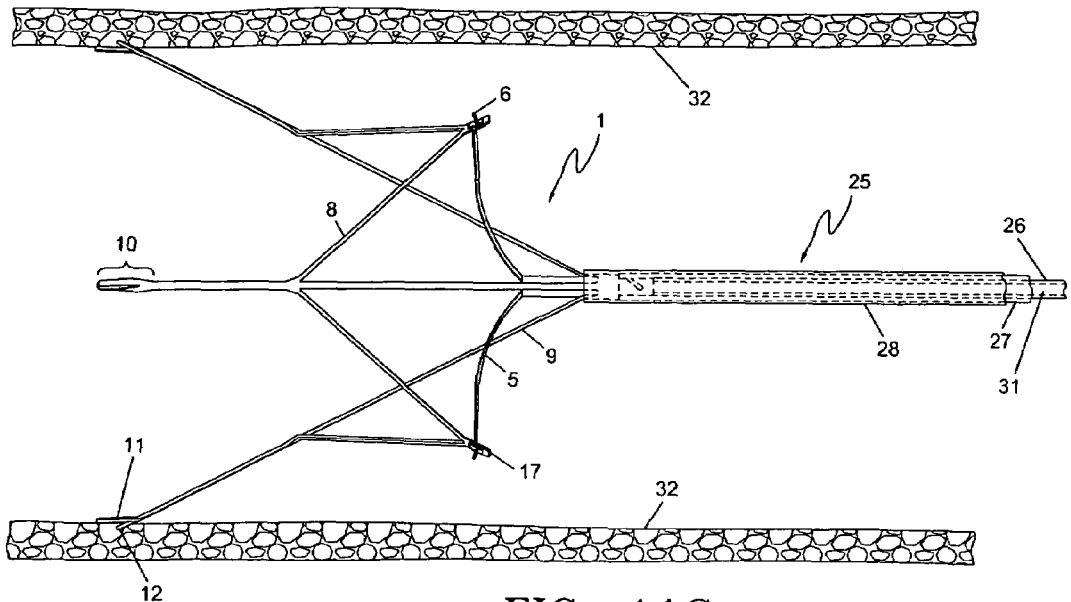

FIG. 11C illustrates the second deployment step in which the remaining portions of the filter 1 are deployed. Although not apparent in FIG. 11C due to the spatial orientation of the device 1, the barbs 6 are in contact with the vessel wall 32. In the second deployment step, the inner member 26 is advanced causing the control strut subassembly 3 to also advance and expand outwardly to contact vessel 32. This movement allows the alignment struts 8 to expand radially outward until the barbs 6 engage the vessel wall at an angle perpendicular to the longitudinal axis of the vessel.

Figure 11D:
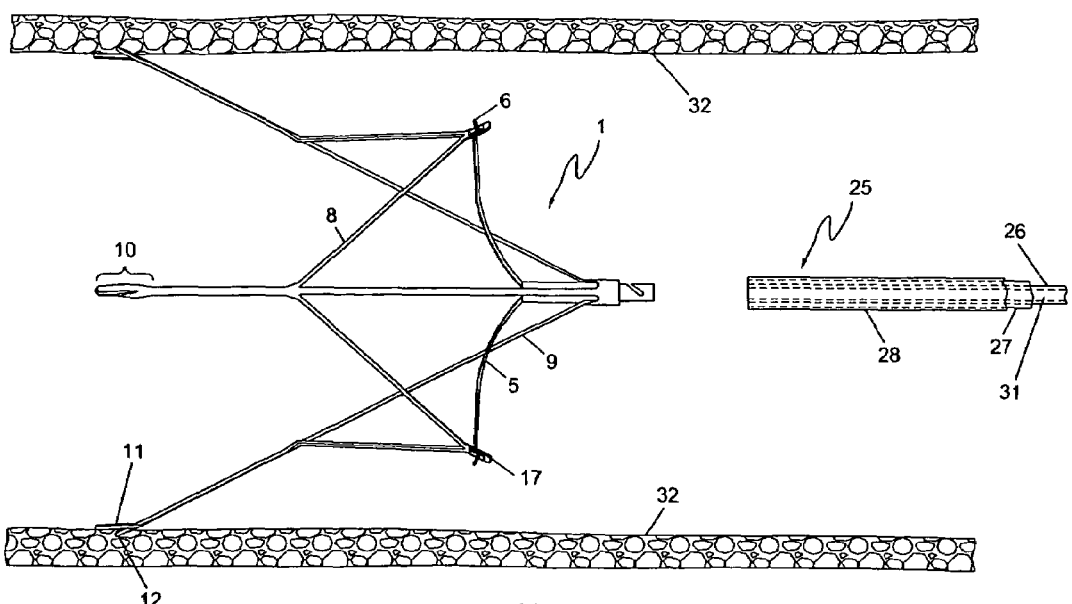

FIG. 11D depicts the filter 1 in its fully deployed configuration after detachment from the deployment device 25. Various detachment mechanisms may be used to release the filter from the deployment system 25. Once disconnected, the device 1 may not be repositioned but may be retrieved using a retrieval system, as will be explained below.

Advantageously, this staged deployment method allows the device to be repositioned after either steps one or two until the deployment system is physically detached from the filter. If the physician needs to reposition the device 1 after the barbs 12 have engaged but prior to full filter deployment, the outer deployment tube 28 may be advanced to enclose and re-collapse the filter legs 9. The barbs 12 disengage from the wall 32 as the device 1 is drawn back into the deployment device 25. In one aspect of the invention, barb 12 disengagement is achieved at an angle equivalent to the engagement angle, whereby minimizing vessel wall trauma.

The outer deployment tube 25 thus control both the deployment and if desired the recapture of the filter legs 9. The filter may be repositioned before or after the wall-engaging portion 10 have engaged the vena cava wall 32. In addition, the filter legs 9 do not spring open suddenly, but rather may be gradually and controllably deployed.

If repositioning of the device 1 is necessary after complete deployment but prior to disengagement from the delivery system, the inner member 26 may be retracted causing the barbs 6 of control struts 5 to be drawn out of the wall 32. Further retraction will result in control strut 5 collapse and withdrawal into device 25. Then the outer deployment tube 28 may be advanced to enclose and re-collapse the filter legs 9 if desired.

FIGS. 11A-11D depict a deployment of the filter using a jugular vein approach. A femoral vein approach for deployment may sometimes be preferred. The vena cava filter of the current invention may be deployed from either approach. With the femoral approach, the filter is positioned within the delivery sheath in the opposite longitudinal orientation so that the hub end of the filter will be deployed first. Specifically, the control struts and interconnecting alignment struts are deployed into the vessel first. The filter legs are then deployed. The delivery device is then detached as previously described.

Thus, in a novel aspect of the current invention, a vena cava filter device is provided that is easy to deploy through a small delivery system using either a femoral or jugular approach and can be repositioned within the vessel after partial or even full deployment. Thus, the staged deployment design of this invention provides the user with not only a small, simple system that features controlled deployment from different approaches but provides the option of repositionability at each deployment step.

Figure 12A:
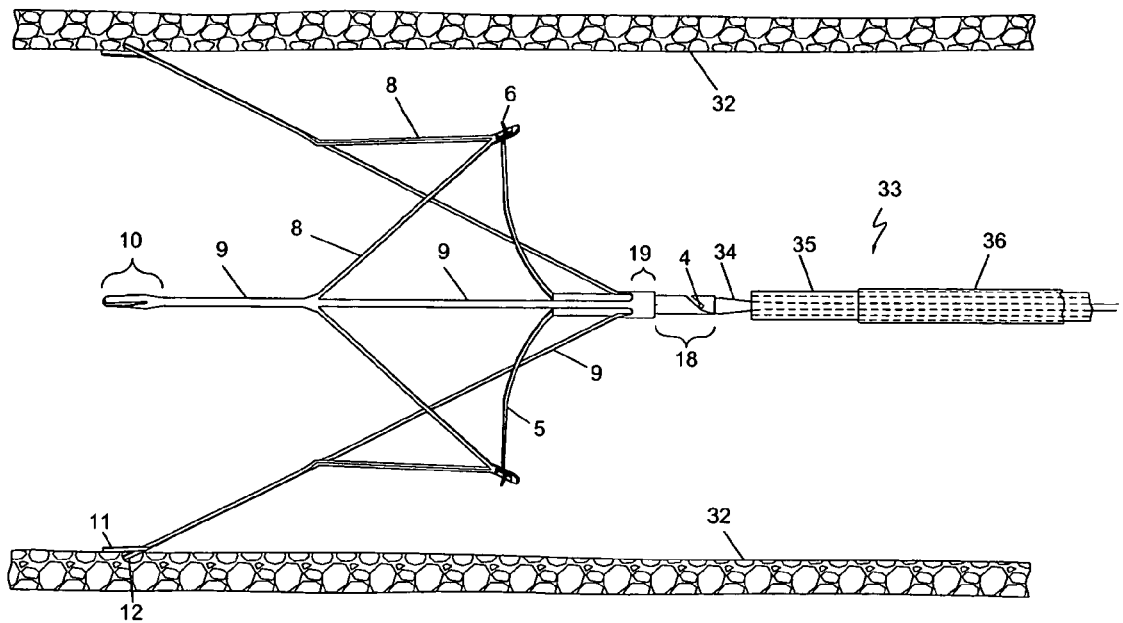
FIGS. 12A through 12D illustrate a method of retrieving the vena cava filter from the vessel.

Methods of device retrieval will now be discussed with reference to FIGS. 12A through 12D. FIG. 12A illustrates the first step in retrieval of the fully deployed filter 1 from within a vena cava. A standard sheath retrieval system 33 is comprised of a snare wire or loop 34, an inner retrieval tube 35 and an outer retrieval tube 36. In FIG. 12A, the snare wire 34 has been positioned within the slot of the retrieval hook 4 of the non-slotted section 18 of the control strut subassembly 3.

Figure 12B:
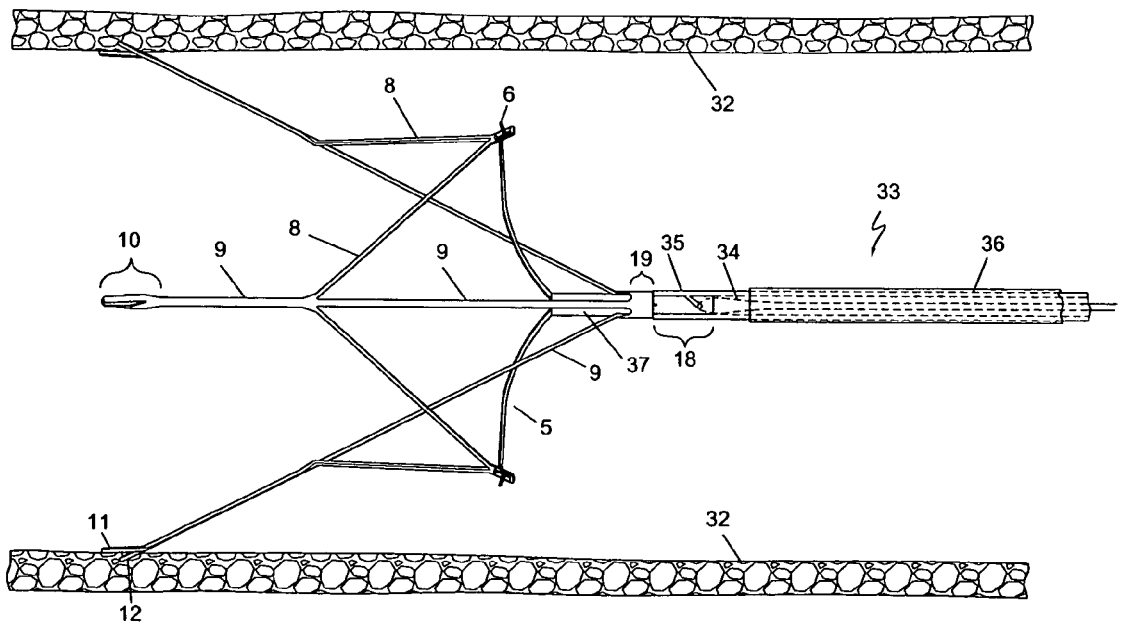

Referring now to FIG. 12B, the inner retrieval tube 35 is advanced over the snare 34 and the non-slotted section 18 of the control strut subassembly 3 until the end of the inner retrieval tube 35 abuts up against the downstream edge of the non-slotted section 19 of the filtering cone/alignment strut subassembly 2.

Figure 12C:
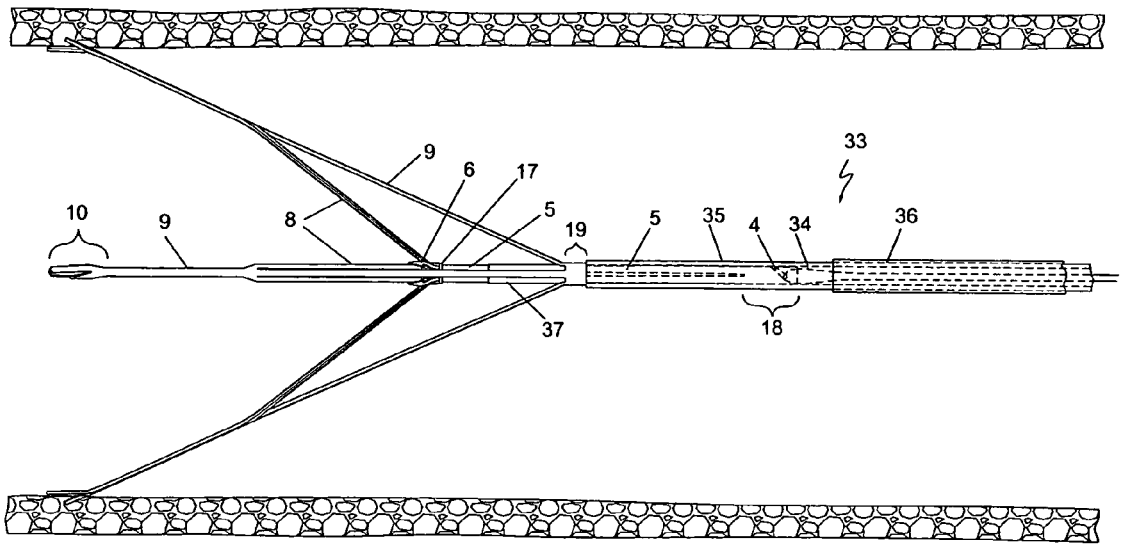

FIG. 12C depicts the retrieval step of collapsing the control struts 5 and alignment struts 8. To activate the collapse of these filter components, the snare wire 34 is retracted, causing retraction of the inner tubular subassembly 3. Retraction of the subassembly 3 in turn causes the control struts 5 to be drawn toward the center of the vessel 32, disengaging the barbs 6 from the vessel wall at an angle perpendicular to the longitudinal axis of the vessel. The inner cannula 37 facilitates retraction by directing the collapsing force of the alignment struts 8 inwardly instead of longitudinally. Because the barbs 6 of control struts 5 are interconnected to the alignment struts 8 through barb-receiving holes 7, the inward radial movement of the control struts causes a corresponding radial movement of the alignment struts 8.

Further retraction of the snare wire 34 results in the complete collapse of the control strut subassembly 3, as shown in FIG. 12C. As the control struts 5 are drawn inwardly to the center of the vessel, the interconnected alignment struts 8 are also drawn inwardly by the retraction force of the control struts 5. The apices 17 of alignment struts 8 will be drawn inward until they are in completely aligned with the center longitudinal axis of the device as shown in FIG. 12C.

Figure 12D:
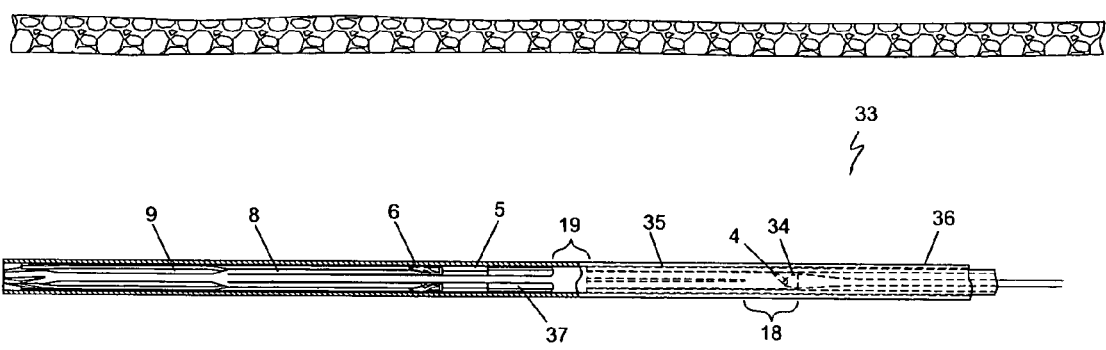

FIG. 12D depicts the collapsed filter device 1 totally enclosed within the retrieval sheath device 33. To complete the collapse the device 1, the outer tube 36 is independently advanced over the downstream portion of the filter legs 9. Further advancement of the outer sheath causes disengagement of wall-engaging portion 10 and complete collapse of the legs 9. Alternatively, retraction of the snare wire will cause collapse of the filter legs 9.

Thus, the current invention provides a conical filter design incorporating stabilizing and centering alignment struts with a control strut mechanism for disengaging the alignment struts from the vessel wall and inwardly radially collapsing them into a profile that can easily be deployed and removed from the body using standard interventional devices.

Other configurations and methods of creating a retrievable vena cava filter are also within the scope of this invention. Modifications to the details illustrated in this disclosure, including filter and component shapes, barb designs, dimensions, materials, methods of construction and methods of use are within the scope of this invention. Accordingly, the scope of the invention is not limited to the foregoing specification, but instead is given by the appended claims along with their full range of equivalents.

What is claimed is:

1. A retrievable blood clot filter having an axis, a primary hub, a set of filter struts extending from said primary hub, and a set of alignment struts having first and second ends and being connected to the filter struts, comprising:
   a secondary hub; and
   a plurality of connector elements, each of said connector elements extending from said secondary hub to form a juncture with said second end of one of said alignment struts, said first end of each alignment strut being connected to one of said filter struts at a position upstream of said primary hub, movement of said secondary hub causing said connector elements to move said alignment struts radially inward;
   wherein the alignment struts are connected to the filter struts at a position to cause substantially the only contact between the alignment struts and a vascular wall to be at said junctures.

2. The retrievable blood clot filter of claim 1 wherein:
   substantially the only contacts between the retrievable blood clot filter and the vascular wall are at radially outward ends of the filter struts and at said junctures.

3. The retrievable blood clot filter of claim 2 wherein:
   said primary hub is tubular and said secondary hub moves within said primary hub.

4. The retrievable blood clot filter of claim 1 wherein:
   said primary hub is tubular and said secondary hub moves within said primary hub.

5. The retrievable blood clot filter of claim 1 wherein the secondary hub includes a retrieval hook.

6. A retrievable blood clot filter having an axis and a primary hub comprising:
   a plurality of filter struts extending axially from the primary hub, said filter struts having radially outward ends,
   a plurality of alignment struts, each of said alignment struts having a first end attached to one of said filter struts at a position upstream of said primary hub and having a second end,
   a secondary hub axially movable relative to said primary hub,
   a plurality of connector elements, each of said connector elements extending from said secondary hub to form a juncture with said second end of one of said alignment struts, axial movement of said secondary hub causing said connector elements to pull said alignment struts radially inward;
   wherein the alignment struts are connected to the filter struts at a position to cause substantially the only contact between the alignment struts and a vascular wall to be at the second ends of the alignment struts.

7. The retrievable blood clot filter of claim 6 wherein:
   said secondary hub is movable within said primary hub.

8. The retrievable blood clot filter of claim 7 wherein:
   said first end of each of said alignment struts is connected to a first end of an adjacent alignment strut, and
   said second end of each of said alignment struts is connected to a second end of an adjacent alignment strut.

9. The retrievable blood clot filter of claim 7 further comprising:

a first set of barbs located at least at some of the junctures of said connector elements and said alignment struts, the direction of said barbs having a primary radial component.

10. The retrievable blood clot filter of claim 9 wherein:
said first end of each of said alignment struts is connected to a first end of an adjacent alignment strut, and
said second end of each of said alignment struts is connected to a second end of an adjacent alignment strut.

11. The retrievable blood clot filter of claim 6 wherein:
the only contacts between the filter and the vascular wall are at the radially outward ends of the filter struts and at said junctures.

12. The retrievable blood clot filter of claim 11 wherein:
said first ends of said alignment struts are connected to an intermediate zone of said filter struts.

13. The retrievable blood clot filter of claim 11 wherein:
said connector elements extend over a zone between said filter struts to provide additional filtering.

14. The retrievable blood clot filter of claim 11 wherein:
said secondary hub is movable within said primary hub.

15. The retrievable blood clot filter of claim 14 further comprising:
a first set of barbs located at least at some of the junctures where said connector elements and said alignment struts are connected together, the direction of said barbs having a primary radial component.

16. The retrievable blood clot filter of claim 14 wherein:
said first end of each of said alignment struts is connected to a first end of an adjacent alignment strut, and
said second end of each of said alignment struts is connected to a second end of an adjacent alignment strut.

17. The retrievable blood clot filter of claim 14 wherein:
said first ends of said alignment struts are connected to an intermediate zone of said filter struts.

18. The retrievable blood clot filter of claim 17 wherein:
said first end of each of said alignment struts is connected to a first end of an adjacent alignment strut, and
said second end of each of said alignment struts is connected to a second end of an adjacent alignment strut.

19. The retrievable blood clot filter of claim 17 further comprising:
a first set of barbs located at least at some of the junctures where said connector elements and said alignment struts are connected together, the direction of said barbs having a primary radial component.

20. The retrievable blood clot filter of claim 19 wherein:
said connector elements extend over a zone between said filter struts to provide additional filtering.

21. The retrievable blood clot filter of claim 11 further comprising:
a first set of barbs located at least at some of the junctures of said connector elements and said alignment struts, the direction of said barbs having a primary radial component.

22. The retrievable blood clot filter of claim 21 wherein:
said first end of each of said alignment struts is connected to a first end of an adjacent alignment strut, and
said second end of each of said alignment struts is connected to a second end of an adjacent alignment strut.

23. The retrievable blood clot filter of claim 6 further comprising:
a first set of barbs located at least at some of the junctures of said connector elements and said alignment struts, the direction of said barbs having a primary radial component.

24. The retrievable blood clot filter of claim 23 further comprising:
a second set of barbs located at radially outward ends of at least some of said filter struts, the direction of said barbs having a primary axial component and a lesser radial component; and
a support foot adjacent to at least some of said second set of barbs to limit the extent that said barbs extend into the vascular wall.

25. The retrievable blood clot filter of claim 6 wherein:
said first end of each of said alignment struts is connected to a first end of an adjacent alignment strut, and
said second end of each of said alignment struts is connected to a second end of an adjacent alignment strut.

26. The retrievable blood clot filter of claim 6 wherein:
said filter struts and said alignment struts substantially overlap in an axial direction.

27. A retrievable blood clot filter having an axis and a primary hub and having a deployed state and a retractable state, comprising:
a plurality of filter struts extending axially from said primary hub, said filter struts having radially outward upstream ends,
a plurality of alignment struts, each of said alignment struts having an upstream end attached to one of said filter struts at a position upstream of said primary hub and having a radially outward downstream end,
said filter struts and said alignment struts substantially overlapping in an axial direction,
a secondary hub axially movable relative to said primary hub, and
a plurality of connector elements, each of said connector elements extending from said secondary hub to form a juncture with a downstream end of one of said alignment struts, axial movement of said secondary hub causing said connector elements to pull said alignment struts radially inward into the retractable state.

28. The retrievable blood clot filter of claim 27 wherein:
said upstream ends of said alignment struts are connected to intermediate positions on said filter struts so that when in the deployed state, substantially the only contact between the filter and a vascular wall are the upstream ends of the filter struts and said junctures.

29. The retrievable blood clot filter of claim 28 wherein:
said downstream end of each of said alignment struts is connected to a downstream end of an adjacent alignment strut and said upstream end of each of said alignment struts is connected to an upstream end of an adjacent alignment strut.

30. The retrievable blood clot filter of claim 27 wherein:
said downstream end of each of said alignment struts is connected to a downstream end of an adjacent alignment strut and said upstream end of each of said alignment struts is connected to an upstream end of an adjacent alignment strut.

31. The retrievable blood clot filter of claim 27 further comprising:
a first set of barbs located at least at some of the attachment points between said connector elements and said downstream ends of said alignment struts, the direction of said barbs in the deployed state having a primary radial component.

32. The retrievable blood clot filter of claim 31 further comprising:
a second set of barbs, each of said barbs located at upstream ends of said filter struts, the direction of said barbs in the deployed state having a primary axial component and a lesser radial component; and a support foot adjacent to at least some of said second set of barbs to limit the extent that said barbs extend into a vascular wall.

33. The retrievable blood clot filter of claim 32 wherein:
said first and second sets of barbs are substantially the sole engagement between the filter and the vascular wall in the deployed state.

34. The retrievable blood clot filter of claim 27 wherein:
said secondary hub is slidable within said primary hub.

35. The retrievable blood clot filter of claim 27 wherein:
said upstream ends of said filter struts and said downstream ends of said alignment struts are substantially the sole contacts between the filter and a vascular wall in the deployed state.

* * * * *